United States Patent
Inoue et al.

(10) Patent No.: US 7,943,624 B2
(45) Date of Patent: *May 17, 2011

(54) PYRIDINYLPYRAZOLOPYRIMIDINONE DERIVATIVES AS PDE 7 INHIBITORS

(75) Inventors: Hidekazu Inoue, Osaka (JP); Hidenobu Murafuji, Osaka (JP); Yasuhiro Hayashi, Osaka (JP)

(73) Assignee: Asubio Pharma Co. Ltd., Tokyo (JP)

( * ) Notice: Subject to any disclaimer, the term of this patent is extended or adjusted under 35 U.S.C. 154(b) by 690 days.

This patent is subject to a terminal disclaimer.

(21) Appl. No.: 11/748,421

(22) Filed: May 14, 2007

(65) Prior Publication Data

US 2007/0270419 A1 Nov. 22, 2007

Related U.S. Application Data

(63) Continuation of application No. 10/560,386, filed as application No. PCT/JP2004/008643 on Jun. 11, 2004, now abandoned.

(30) Foreign Application Priority Data

Jun. 13, 2003 (JP) .................................. 2003-170094

(51) Int. Cl.
  *C07D 487/04* (2006.01)
  *A61K 31/519* (2006.01)
  *A61P 37/02* (2006.01)
  *A61P 29/00* (2006.01)

(52) U.S. Cl. ..................................... 514/262.1; 544/262

(58) Field of Classification Search .................. 544/262; 514/262.1

See application file for complete search history.

(56) References Cited

U.S. PATENT DOCUMENTS

| | | | |
|---|---|---|---|
| 5,541,187 A | 7/1996 | Bacon et al. | |
| 6,407,114 B1 | 6/2002 | Bunnage et al. | |
| 6,613,778 B1 | 9/2003 | Eggenweiler et al. | |
| 6,627,651 B1 | 9/2003 | Shiraishi et al. | |
| 6,677,335 B1 | 1/2004 | Bunnage et al. | |
| 6,737,436 B1 | 5/2004 | Eggenweiler et al. | |
| 2004/0138279 A1 | 7/2004 | Eggenweiler et al. | |

FOREIGN PATENT DOCUMENTS

| | | |
|---|---|---|
| DE | 19950647 | 4/2001 |
| EP | 349239 | 1/1990 |
| EP | 463756 | 1/1992 |
| EP | 526004 | 2/1993 |
| EP | 636626 | 2/1995 |
| EP | 0995750 | 4/2000 |
| EP | 995751 | 4/2000 |
| EP | 1092720 | 4/2001 |
| EP | 1176147 | 1/2002 |
| JP | 08-253484 | 10/1996 |
| WO | WO 00/68203 | 11/2000 |
| WO | WO 01/32618 | 5/2001 |
| WO | WO 01/34601 | 5/2001 |
| WO | WO 01/74786 | 10/2001 |
| WO | WO 01/98274 | 12/2001 |
| WO | WO 02/28847 | 4/2002 |
| WO | WO 02/40450 | 5/2002 |
| WO | WO 02/074754 | 9/2002 |
| WO | WO 02/087513 | 11/2002 |
| WO | WO 02/088080 | 11/2002 |
| WO | WO 02/102315 | 12/2002 |

OTHER PUBLICATIONS

Barnes et al. "Synthesis and Structure-Activity Relationships of Guanine Analogues as Phosphodiesterase 7 (PDE7) Inhibitors." Bioorg. Med. Chem. Lett. (2001), vol. 11, pp. 1081-1083.

Martinez et al. "Benyzl Derivatives of 2,1,3-Benzo- and Benzothieno[3,2-a]thiadiazine 2,2-Dioxides: First Phosphodiesterase 7 Inhibitors." J. Med. Chem. (2000), vol. 43, pp. 683-689.

Castro et al. "CoMFA of benzyl derivatives of 2,1,3-benzo and benzothieno[3,2-a]thiadiazine 2,2-dioxides: clues for the design of phosphodiesterase 7 inhibitors." Eur. J. Med. Chem. (2001), vol. 36, pp. 333-338.

International Preliminary Report on Patentability for International Application No. PCT/JP2004/008643, mail date: Dec. 29, 2005.

C. Lugnier, Pharma & Therap; 2006; 109; 366-398.

*Primary Examiner* — Susanna Moore
(74) *Attorney, Agent, or Firm* — Hunton & Williams LLP

(57) ABSTRACT

To provide the compounds inhibiting PDE 7 selectively, and therefore, enhance cellular cAMP level. Consequently, the compound is useful for treating various kinds of disease such as allergic disease, inflammatory disease or immunologic disease. The compound is pyridinylpyrazolo-pyrimidinone compound represented by the following formula (IA) or (IB):

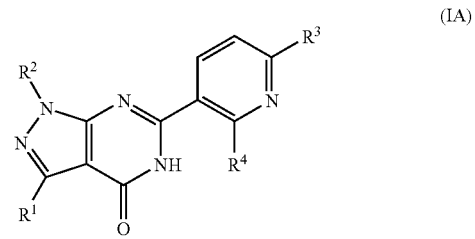

(IA)

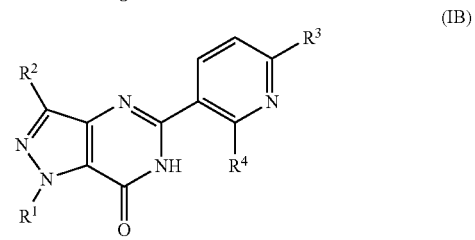

(IB)

especially, $R^1$ is cyclohexyl or cycloheptyl group, $R^2$ is methyl; $R^3$ is a group: $-NR^5R^6$ or $-S(O)_{0-2}R^8$; hydrogen atom; nitro group; cyano group; a halogen atom; heteroaryl group; and $R^4$ is methoxy or ethoxy group.

8 Claims, No Drawings

PYRIDINYLPYRAZOLOPYRIMIDINONE DERIVATIVES AS PDE 7 INHIBITORS

CROSS-REFERENCE TO RELATED APPLICATIONS

This patent application is a continuation of U.S. application Ser. No. 10/560,386, filed on Dec. 13, 2005 now abandoned, which is the U.S. National Stage application of International Application No. PCT/JP2004/008643, filed on Jun. 11, 2004, which claims the benefit of Japanese Patent Application No. 2003-170094, filed on Jun. 13, 2003, each of which is incorporated by reference in their entireties.

BACKGROUND OF THE INVENTION (i) Field of the Invention

The present invention relates to pyridinylpyrazolopyrimidinone compounds, pharmaceutically acceptable salts and solvates thereof, having selective PDE 7 (phosphodiesterase VII) inhibiting effect. These compounds are effective compounds for treating various kinds of disease such as allergic disease, inflammatory disease and immunologic disease.

(ii) Description of the Related Art

A cyclic AMP (cAMP) or cyclic GMP (cGMP), which is an intracellular second messenger substance, is decomposed and inactivated by phosphodiesterase (PDE 1 to PDE 11). The PDE 7 selectively decomposes cAMP, and is characterized as an enzyme not decomposed by rolipram. Rolipram is a selective inhibitor of PDE 4 which decomposes cAMP.

It is suggested that PDE 7 plays an important role for activating T cells (Beavo, et al., Science, 283, 848 (1999)), and well known that activating of T-cell is concerned with the exacerbation of allergic disease, inflammatory disease or immunologic disease. These diseases are for example bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, graft versus host disease (GVH disease), and restenosis after angioplasty. [*J. Allergy Clin. Immunol.*, 2000 November; 106(5 Suppl.): S221-6; *Am. J. Respir. Crit. Care Med.*, 1996 February; 153(2): 629-32; *Am. J. Respir. Crit. Care Med.*, 1999 November; 160(5 Pt 2): S33-7; *Clin. Exp. Allergy*, 2000 February; 30(2): 242-54; *Hosp. Med.*, 1998 July; 59(7): 530-3; *Int. Arch. Allergy Immunol.*, 1998 March; 115(3): 179-90; *J. Immunol.*, 1991 February 15; 146(4): 1169-74; *Osteoarthritis Cartilage*, 1999 July; 7(4): 401-2; *Rheum. Dis. Clin. North Am.*, 2001 May; 27(2): 317-34; *J. Autoimmun.*, 2001 May; 16(3): 187-92; *Curr. Rheumatol. Rep.*, 2000 February; 2(1): 24-31; *Trends Immunol.*, 2001 January; 22(1): 21-6; *Curr. Opin. Immunol.*, 200 August; 12(4): 403-8; *Diabetes Care*, 2001 September; 24(9): 1661-7; *J. Neuroimmunol.*, 2000 November 1; 111(1-2): 224-8; *Curr. Opin. Immunol.*, 1997 December; 9(6): 793-9; *JAMA*, 1999 September 15; 282(11): 1076-82; *Semin. Cancer Biol.*, 1996 April; 7(2): 57-64; *J. Interferon Cytokine Res.*, 2001 April; 21(4): 219-21].

Therefore, it is considered that a compound having PDE 7 inhibiting effect is useful for treating various kinds of disease such as allergic disease, inflammatory disease or immunologic disease concerned with T cells.

There has been proposed many compounds selectively inhibit PDE 7. These are for example, imidazopyridine derivatives (International Patent Publication WO 01/34601), dihydropurine derivatives (International Patent Publication WO 00/68203), pyrrole derivatives (International Patent Publication WO 01/32618), benzothiopyranoimidazolone derivatives (DE Patent 19950647), heterocyclic compounds (International Patent Publications WO 02/88080; 02/87513), quinazoline and pyridopyrimidine derivatives (International Patent Publication WO 02/102315), spiro tricyclic compounds (International Patent Publication WO 02/74754), thiazole and oxathiazole derivatives (International Patent Publication WO 02/28847), sulfonamide derivatives (International Patent Publication WO 01/98274), heterobiarylsulfonamide derivatives (International Patent Publication WO 01/74786), dihydroisoquinoline derivatives (International Patent Publication WO 02/40450), guanine derivatives (*Bioorg. Med. Chem. Lett.*, 11(2001), 1081), benzothiadiazine derivatives (*J. Med. Chem.*, 43(2000), 683) and benzothienothiadiazine derivatives (*Eur. J. Med. Chem.*, 36(2001), 333). However, no curative medicines having PDE 7 inhibiting effect as main pharmacological mechanism have developed up to now.

Though some pyrazolopyrimidinone derivatives as cGMP specified PDE inhibitor have been known (For examples: EP 463756; EP 526004; EP 349239; EP 636626; EP 995751; and Japanese Patent Publication No. Hei8-25384), there is no suggestion that these compounds have PDE 7 inhibiting effect.

Therefore, the purpose of the present invention is to provide novel compounds having PDE 7 inhibiting effect, and PDE 7 inhibiting composition containing the same as an active ingredient.

The compounds of the present invention inhibit PDE 7 selectively, and therefore, enhance cellular cAMP level. Consequently, the compounds of the present invention are useful for treating various kinds of disease such as allergic disease, inflammatory disease or immunologic disease.

For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, GVH disease, restenosis after angioplasty.

SUMMARY OF THE INVENTION

Through extensive investigations of researching compounds having the capabilities of inhibiting PDE 7, the present inventors discovered that the compounds having pyridinylpyrazolopyrimidinone skeleton in the molecular represented by the formula (IA) or (113) mentioned below possess potent and selective PDE 7 inhibiting effect, and therefore, completed the present invention.

Accordingly, as one aspect of the present invention, it is provided pyridinylpyrazolopyrimidinone compounds represented by the following formula (IA) or (IB):

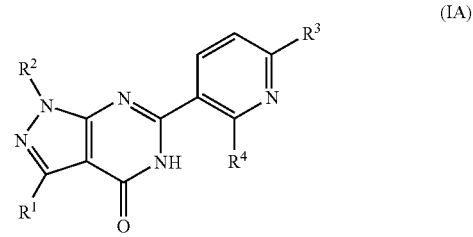

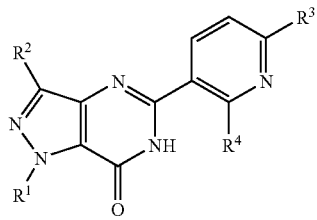
(IB)

wherein:

$R^1$ is substituted or unsubsituted $C_3$-$C_8$ cycloalkyl group or tert-butyl group;

$R^2$ is a hydrogen atom or $C_1$-$C_3$ alkyl group;

$R^3$ is a group: —$NR^5R^1$, —$C(=O)R^1$ or —$S(O)_{0-2}R^1$;

$R^4$ is a hydrogen atom or $C_1$-$C_3$ alkoxy group which is unsubstututed or substituted by one or more fluorine atom(s);

$R^5$ and $R^6$ are, same or different from each other, a hydrogen atom, substituted or unsubsituted $C_1$-$C_6$ alkyl group, substituted or unsubsituted acyl group, substituted or unsubsituted heterocycloalkyl group, and substituted or unsubsituted heterocycloalkyl ring is formed with nitrogen atom which is binding $R^5$ and $R^6$;

$R^7$ is a group: —$OR^9$ or —$NR^5R^6$;

$R^8$ is a hydrogen atom, a halogen atom, a group: —$NR^5R^6$, substituted or unsubsituted $C_1$-$C_6$ alkyl group, or substituted or unsubsituted aryl group;

$R^9$ is a hydrogen atom or substituted or unsubsituted $C_1$-$C_6$ alkyl group; or pharmaceutically acceptable salts or solvates thereof.

Still another aspect of the present invention, it is provided PDE 7 inhibiting composition containing the pyridinylpyrazolopyrimidinone compounds mentioned above, or pharmaceutically acceptable salts or solvates thereof as an active ingredient.

DETAILED DESCRIPTION OF THE INVENTION

The present invention will now be explained more specifically as following.

The term "$C_1$-$C_3$ alkyl group" of the present invention includes a straight or branched-chained alkyl group having 1 to 3 carbon atoms, such as methyl, ethyl and propyl group, and the term "$C_1$-$C_6$ alkyl group" of the present invention means a straight or branched-chained alkyl group having 1 to 6 carbon atoms such as methyl, ethyl, propyl, butyl, pentyl and hexyl group. The term "$C_3$-$C_8$ cycloalkyl group" of the present invention includes a cycloalkyl group having 3 to 8 carbon atoms such as cyclopropyl, cyclobutyl, cyclopentyl, cyclohexyl and cyclooctyl.

The term "heterocycloalkyl group" is 3 to 7 membered heterocyclic group containing the same or different 1 to 4 hetero atom(s) such as oxygen, nitrogen or sulfur atom(s), and examples may include pyrrolidinyl, piperidinyl, piperazinyl, homopiperazinyl, tetrahydrofuryl, tetrahydropyranyl, morpholinyl and azetidinyl.

The term "$C_1$-$C_3$ alkoxy group" means alkoxy group having 1 to 3 carbon atoms and examples include methoxy, ethoxy and propoxy. The term "acyl group" means acyl group having 1 to 8 carbon atoms, and examples include formyl, acetyl, propionyl, butanoyl, pentanoyl, benzoyl and toluoyl. The "halogen atom" includes fluorine, chlorine, bromine and iodine.

The term "aryl group" is phenyl, naphthyl, biphenyl group which is consisted by 6 to 12 carbon atoms, and the term "heteroaryl group" is 5 to 7 membered monocyclic or polycyclic group thereof containing 2 to 8 carbon atoms and the same or different 1 to 4 hetero atom(s) such as oxygen, nitrogen, sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl pyridazinyl and pyrimidinyl.

Examples of suitable substituent of "substituted or unsubstituted $C_1$-$C_6$ alkyl group" include hydroxyl group and halogen atom, and examples of suitable substituent of "substituted or unsubstituted acyl group" include halogen atom and nitro group. Further, examples of suitable substituent of "substituted or unsubstituted aryl group" include $C_1$-$C_3$ alkyl, halogen atom, amino group, acyl group, amide group, hydroxyl group, acylamino group, carboxyl group and sulfonyl group. Examples of suitable substituent of "substituted or unsubstituted $C_3$-$C_8$ cycloalkyl group" is $C_1$-$C_3$ alkyl, hydroxyl group and oxo group, and examples of suitable substituent of "substituted or unsubstituted heterocycloalkyl group" may include carboxy group, acyl group, alkoxy group, amino group, alkylamino group, acylamino group, hydroxyl group, oxo group, ethylenedioxy group, methyl group, ethyl group and hydroxyethyl group.

Preferable compounds of the formula (IA) and (IB) of the present invention include the compounds wherein $R^1$ is cyclohexyl group or cycloheptyl group; $R^2$ is methyl group; $R^3$ is the group —$NR^5R^6$ or —$S(O)_{0-2}R^8$; and $R^4$ is methoxy or ethoxy group.

The compounds of the formula (IA) and (IB) of the present invention may exist in the tautomeric mixtures, the tautomeric isomers per se, and the mixture thereof. Furthermore, the radiolabelled compounds of the formula (IA) and (IB) shall be included within the scope of the compounds of the present invention.

The compounds of the present invention may contain one or more asymmetric carbon atom and therefore, the compounds of the present invention may exist as optically isomer of (R)-form or (S)-form, racemic forms, as well as diastereomers. Further, the compounds of the present invention may exist as geometrical isomer such as (Z)-form or (E)-form due to the double bond in the substituent. Therefore, the compounds of the present invention should include these isomers per se as well as the isomeric mixtures thereof.

The compounds of the present invention may form acid additional salt thereof with various acids. Examples of the acid additional salt include the salts with inorganic acid such as hydrochloric acid, hydrobromic acid, hydriodic acid, sulfuric acid, nitric acid and phosphoric acid; salts with organic acid such as formic acid, acetic acid, propionic acid, oxalic acid, malonic acid, succinic acid, fumaric acid, maleic acid, lactic acid, malic acid, citric acid, tartaric acid, benzoic acid, picric acid, methanesulfonic acid, toluenesulfonic acid, benzenesulfonic acid, trichloroacetic acid, trifluoroacetic acid, asparaginic acid and glutamic acid.

The compounds of the present invention may form pharmaceutically acceptable metal salts by treating with various kinds of metal, especially alkali metal or alkali earth metal. These salts may include sodium salt, potassium salt and calcium salt. Further, the compounds of the present invention may include hydrate or solvate with water, ethanol or isopropanol, and polymorphisms thereof.

The following compounds are preferable pyridinylpyrazolo-pyrimidinone compounds of the formula (IA) or (IB).

1-cyclohexyl-5-{2-methoxy-6-[(4-methylphenyl)sulfanyl]-3-pyridinyl}-3-methyl-1,6-dihydro-7H-pyrazolo[4,3-d]pyrimidin-7-one;

1-cyclohexyl-5-{2-methoxy-6-[(4-methylphenyl)sulfonyl]-3-pyridinyl}-3-methyl-1,6-dihydro-7H-pyrazolo[4,3-d]pyrimidin-7-one;

3-cyclohexyl-6-{2-methoxy-6-[(4-methylphenyl)sulfanyl]-3-pyridinyl}-1-methyl-1,5-dihydro-4H-pyrazolo[3,4-d]pyrimidin-4-one;

3-cyclohexyl-6-{2-methoxy-6-[(4-methylphenyl)sulfonyl]-3-pyridinyl}-1-methyl-1,5-dihydro-4H-pyrazolo[3,4-d]pyrimidin-4-one;

1-cyclohexyl-5-[2-methoxy-6-(4-methyl-1-piperazinyl)-3-pyridinyl]-3-methyl-1,6-dihydro-7H-pyrazolo[4,3-d]pyrimidin-7-one;

1-cyclohexyl-5-[2-methoxy-6-(4-morpholinyl)-3-pyridinyl]-3-methyl-1,6-dihydro-7H-pyrazolo[4,3-d]pyrimidin-7-one;

1-cyclohexyl-5-[2-methoxy-6-(4-methyl-1,4-diazepan-1-yl)-3-pyridinyl]-3-methyl-1,6-dihydro-7H-pyrazolo[4,3-d]pyrimidin-7-one;

1-cyclohexyl-5-[6-(1,4-dioxa-8-azaspiro[4.5]dec-8-yl)-2-methoxy-3-pyridinyl]-3-methyl-1,6-dihydro-7H-pyrazolo[4,3-d]pyrimidin-7-one;

1-cyclohexyl-5-[2-methoxy-6-(4-oxo-1-piperidinyl)-3-pyridinyl]-3-methyl-1,6-dihydro-7H-pyrazolo[4,3-d]pyrimidin-7-one;

1-cyclohexyl-5-[6-(4-hydroxy-1-piperidinyl)-2-methoxy-3-pyridinyl]-3-methyl-1,6-dihydro-7H-pyrazolo[4,3-d]pyrimidin-7-one;

1-cyclohexyl-5-{2-methoxy-6-[4-(methylamino)-1-piperidinyl]-3-pyridinyl}-3-methyl-1,6-dihydro-7H-pyrazolo[4,3-d]pyrimidin-7-one;

1-cyclohexyl-5-16-[4-(dimethylamino)-1-piperidinyl-2-methoxy-3-pyridinyl]-3-methyl-1,6-dihydro-7H-pyrazolo[4,3-d]pyrimidin-7-one;

6-[6-(4-amino-1-piperidinyl)-2-methoxy-3-pyridinyl]-1-cyclohexyl-3-methyl-1,6-dihydro-7H-pyrazolo[4,3-d]pyrimidin-7-one;

N-{1-[5-(1-cyclohexyl-3-methyl-7-oxo-6,7-dihydro-1H-pyrazolo[4,3-d]-pyrimidin-5-yl)-6-methoxy-2-pyridinyl]-4-piperidinyl} acetamide;

1-cyclohexyl-5-(2-methoxy-3-pyridinyl)-3-methyl-1,6-dihydro-7H-pyrazolo[4,3-d]pyrimidin-7-one;

3-cyclohexyl-6-[6-(1,4-dioxa-8-azaspiro[4.5]dec-8-yl)-2-methoxy-3-pyridinyl]-1-methyl-1,5-dihydro-4H-pyrazolo[3,4-d]pyrimidin-4-one;

3-cyclohexy-6-[2-methoxy-6-(4-oxo-1-piperidinyl)-3-pyridinyl]-1-methyl-1,5-dihydro-4H-pyrazolo[4,3-d]pyrimidin-4-one;

3-cyclohexyl-6-[6-(4-hydroxy-1-piperidinyl)-2-methoxy-3-pyridinyl]-1-methyl-1,5-dihydro-4H-pyrazolo[3,4-d]pyrimidin-4-one;

3-cyclohexyl-6-(2-methoxy-6-[4-(methylamino)-1-piperidinyl]-3-pyridinyl)-1-methyl-1,5-dihydro-4H-pyrazolo[3,4-d]pyrimidin-4-one;

3-cyclohexyl-6-{6-[4-(dimethylamino)-1-piperidinyl]-2-methoxy-3-pyridinyl}-1-methyl-1,5-dihydro-4H-pyrazolo[4,3-d]pyrimidin-4-one;

6-[6-(4-amino-1-piperidinyl)-2-methoxy-3-pyridinyl]-3-cyclohexyl-1-methyl-1,5-dihydro-4H-pyrazolo[3,4-d]pyrimidin-4-one;

N-{1-[5-(3-cyclohexyl-1-methyl-4-oxo-4,5-dihydro-1H-pyrazolo[3,4-d]-pyrimidin-6-yl)-6-methoxy-2-pyridinyl]-4-piperidinyl} acetamide;

1-cyclohexyl-5-(2-methoxy-3-pyridinyl)-3-methyl-1,6-dihydro-7H-pyrazolo[4,3-d]pyrimidin-7-one;

3-cyclohexyl-6-[2-methoxy-6-(4-methyl-1-piperazinyl)-3-pyridinyl]-1-methyl-1,5-dihydro-4H-pyrazolo[3,4-d]pyrimidin-4-one;

3-cyclohexyl-6-[2-methoxy-6-(4-morpholinyl)-3-pyridinyl]-1-methyl-1,5-dihydro-4H-pyrazolo[3,4-d]pyrimidin-4-one;

3-cyclohexyl-6-[2-methoxy-6-(4-methyl-1,4-diazepan-1-yl)-3-pyridinyl]-1-methyl-1,5-dihydro-4H-pyrazolo[3,4-d]pyrimidin-4-one;

3-cyclohexyl-6-[6-(1,4-dioxa-8-azaspiro[4.5]dec-8-yl)-2-methoxy-3-pyridinyl]-1-methyl-1,5-dihydro-4H-pyrazolo[3,4-d]pyrimidin-4-one;

3-cyclohexyl-6-[2-methoxy-6-(4-oxo-1-piperidinyl)-3-pyridinyl]-1-methyl-1,5-dihydro-4H-pyrazolo[3,4-d]pyrimidin-4-one;

3-cyclohexyl-6-[6-(4-hydroxy-1-piperidiny)-2-methoxy-3-pyridinyl]-1-methyl-1,5-dihydro-4H-pyrazolo[3,4-d]pyrimidin-4-one;

3-cyclohexyl-6-{2-methoxy-6-[4-(methylamino)-1-piperidinyl]-3-pyridinyl}-1-methyl-1,5-dihydro-4H-pyrazolo[3,4-d]pyrimidin-4-one;

3-cyclohexyl-6-{6-[4-(dimethylamino)-1-piperidinyl]-2-methoxy-3-pyridinyl}-1-methyl-1,5-dihydro-4H-pyrazolo[3,4-d]pyrimidin-4-one;

6-[6-(4-amino-1-piperidinyl)-2-methoxy-3-pyridinyl]-3-cyclohexyl-1-methyl-1,5-dihydro-4H-pyrazolo[3,4-d]pyrimidin-4-one;

N-{1-[5-(3-cyclohexyl-1-methyl-4-oxo-4,5-dihydro-1H-pyrazolo[3,4-d]-pyrimidin-6-yl)-6-methoxy-2-pyridinyl]-4-piperidinyl} acetamide;

3-cyclohexyl-6-(2-methoxy-6-sulfanyl-3-pyridinyl)-1-methyl-1,5-dihydro-4H-pyrazolo[3,4-d]pyrimidin-4-one;

5-(3-cyclohexyl-1-methyl-4-oxo-4,5-dihydro-1H-pyrazolo[3,4-d]-pyrimidin-6-yl)-6-methoxy-2-pyridinesulfonyl chloride;

3-cyclohexyl-6-{2-methoxy-6-[(4-methyl-1,4-diazepan-1-yl)sulfonyl]-3-pyridinyl}-1-methyl-1,5-dihydro-4H-pyrazolo[3,4-d]pyrimidin-4-one;

1-cyclohexyl-5-{2-methoxy-6-[(4-methylphenyl)sulfinyl]-3-pyridinyl}-3-methyl-1,6-dihydro-7H-pyrazolo[4,3-d]pyrimidin-7-one;

1-cyclohexyl-5-{2-ethoxy-6-[(4-methylphenyl)sulfanyl]-3-pyridinyl}-3-methyl-1,6-dihydro-7H-pyrazolo[4,3-d]pyrimidin-7-one;

1-cyclohexyl-5-{2-ethoxy-6-[(4-methylphenyl)sulfonyl]-3-pyridinyl}-3-methyl-1,6-dihydro-7H-pyrazolo[4,3-d]pyrimidin-7-one;

1-cyclohexy-5-[2-ethoxy-6-(4-methyl-1-piperazinyl)-3-pyridinyl]-3-methyl-1,6-dihydro-7H-pyrazolo[4,3-d]pyrimidin-7-one;

1-cyclohexyl-5-[2-ethoxy-6-(4-methyl-1,4-diazepan-1-yl)-3-pyridinyl]-3-methyl-1,6-dihydro-7H-pyrazolo[4,3-d]pyrimidin-7-one;

1-cyclohexyl-5-[6-(1,4-dioxa-8-azaspiro[4,5]deca-8-yl)-2-ethoxy-3-pyridinyl]-3-methyl-1,6-dihydro-7H-pyrazolo[4,3-d]pyrimidin-7-one;

1-cyclohexyl-5-[2-ethoxy-6-(4-oxo-1-piperidinyl)-3-pyridiny]-3-methyl-1,6-dihydro-7H-pyrazolo[4,3-d]pyrimidin-7-one;

1-cyclohexyl-5-{6-[4-(dimethylamino)-1-piperidinyl]-2-ethoxy-3-pyridinyl}-3-methyl-1,6-dihydro-7H-pyrazolo[4,3-d]pyrimidin-7-one;

1-cyclohexyl-5-{2-ethoxy-6-[4-(methylamino)-1-piperidinyl]-3-pyridinyl}-3-methyl-1,6-dihydro-7H-pyrazolo[4,3-d]pyrimidin-7-one;

1-cyclohexyl-5-[2-ethoxy-6-(4-hydroxy-1-piperidinyl)-3-pyridinyl]-3-methyl-1,6-dihydro-7H-pyrazolo[4,3-d]pyrimidin-7-one.

The compound of the formula (IA) of the present invention can be synthesized by the following methods.

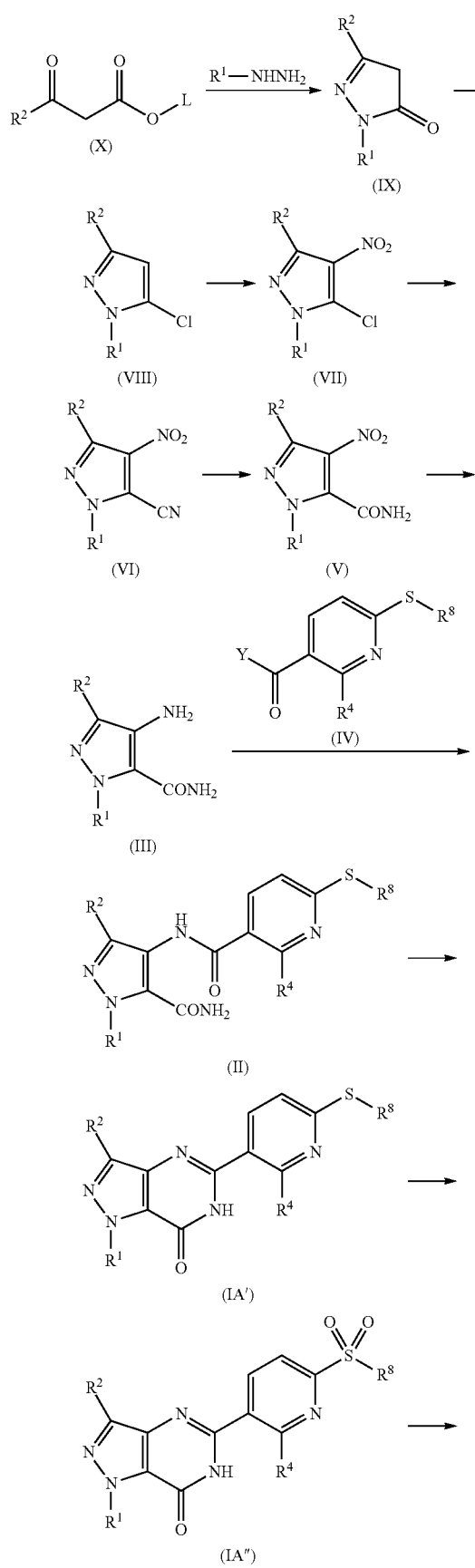
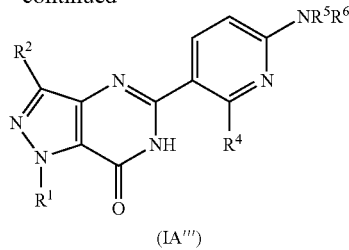

(wherein, $R^1$, $R^2$, $R^4$, $R^5$, $R^6$ and $R^8$ have same meaning mentioned above; L is $C_1$-$C_3$ lower alkyl, and Y is hydroxyl group or halogen atom, preferably chlorine atom)

First, the compound (IX) obtained from the compound (X) by reacting with $R^1NHNH_2$ or salt thereof in accordance with the known method. Namely, the compound (X) is reacted with 1 to 2 equivalent, preferably about 1 equivalent of $R^1NHNH_2$ or salt thereof in the solvent or absent of the solvent at room temperature to 120° C. The solvent to be used in the reaction is inorganic acid aqueous solution such as hydrochloric acid or sulfuric acid; aromatic carbon hydrate such as benzene or toluene; organic acid such as acetic acid; alcohols such as methanol or ethanol; or the mixture solvent there of. After the reaction is completed, inorganic base aqueous solution such as sodium hydroxide aqueous solution is added to the reaction mixture and the mixture is extracted with an organic solvent, which is nonmiscible solvent with water, and the organic layer is washed sequentially with water and saturated saline solution. Then, the compound (IX) can be obtained by removal of the solvent. This compound (IX) can be purified by recrystallization, if necessary.

The compound (X) to be used in this reaction can be commercially available or can be easily prepared from known compounds by using common methods. Further, the compound represent by the formula $R^1NHNH_2$ or salt thereof can also be commercially available or can be easily prepared from known compounds by using common methods (For example: J. Org. Chem., 1981, 46, 5414-5415).

Then, the compound (IX) is converted to the compound (VIII) in accordance with the common method. Namely, the reaction can be conducted by reacting the compound (IX) with 1 to 5 equivalent of halogenate reagent such as phosphorus oxychloride or thionyl chloride in aromatic hydrocarbon solvent such as benzene or toluene, or the absence of the solvent, at room temperature to refluxing temperature of the solvent. After the reaction is completed, the compound (VIII) can be obtained by removal of the solvent.

The obtained compound (VIII) is converted, without further purification, to the compound (VII) by nitration in accordance with the common method. The nitration can be conducted by using nitric acid with sulfuric acid or acetic anhydride at the temperature from −20° to room temperature. After the reaction is completed, the reaction mixture is poured into ice and the resulting precipitate is collected to obtain the purpose compound (VII). This compound (VII) can be purified by recrystallization, if necessary.

Next, the obtained compound (VII) is converted to the compound (VI) in accordance with the common method. Namely, the reaction can be conducted by reacting the compound (VII) with 1 to 3 equivalent metal cyanide such as potassium cyanide or sodium cyanide in a polar solvent such as N,N-dimethylformamide at room temperature to 120° C. After the reaction is completed, water is added to the reaction mixture and the mixture is extracted with an organic solvent, which is nonmiscible solvent with water, and the organic layer is washed sequentially with water and saturated saline solution. Then, the compound (VI) can be obtained by removal of the solvent. This compound (VI) can be purified by chromatography, if necessary.

The obtained compound (VI) is converted to the compound (V) in accordance with the common method. This reaction is hydrolysis reaction of nitrile group converting to the corresponding acid amide group, and various methods are applied. For example, the reaction can be conducted by reacting the compound (VI) with hydrogen peroxide in the presence of base such as sodium hydroxide or potassium carbonate in a solvent at 0° C. to the room temperature. The solvent to be used is water, alcohols such as methanol or ethanol, ethers such as 1,4-dioxane or tetrahydrofuran, or the mixture thereof. After the reaction is completed, the reaction mixture is extracted with an organic solvent, which is nonmiscible solvent with water, and the organic layer is washed sequentially with water and saturated saline solution. Then, the compound (V) can be obtained by removal of the solvent. This compound (V) can be purified by recrystallization, if necessary.

Then, the obtained compound (V) is converted to the compound (III) in accordance with the common method. This reaction is reduction of nitro group converting to the corresponding amino group, and various methods are applied. For example, the reaction can be conducted by reacting the compound (V) with 2 to 10 equivalent of tin(II) chloride in the presence of inorganic acid such as hydrochloric acid at 0° C. to the refluxing temperature. After the reaction is completed, the reaction mixture is neutralized by inorganic base such as sodium hydroxide, and filtrate by Celite®. The obtained filtrate is extracted with an organic solvent, which is nonmiscible solvent with water, and the organic layer is washed sequentially with water and saturated saline solution. Then, the compound (III) can be obtained by removal of the solvent. This compound (III) can be purified by chromatography, if necessary.

The obtained compound (III) is, then, converted to the compound (II) in accordance with the common method. This reaction can be conducted by the reaction of the amine compound (III) with carboxylic compound (IV) to obtain the corresponding acid amide compound (II), and various methods are applied. For example, in the case of the compound (IV) in which Y is halogen atom, preferably chlorine atom, the reaction can be conducted by reacting the compound (III) with 1.0 to 1.5 equivalent, preferably 1.2 equivalent of the compound (IV) in the presence of 1 to 5 equivalent, preferably 2.5 equivalent of tertiary amine such as triethylamine, based on the compound (III), and if necessary in the presence of the catalyst such as 4-dimethylaminopyridine. The reaction can be carried out in the presence of inert solvent such as dichloromethane at 0° C. to the room temperature.

Furthermore, in the case of the compound (IV) in which Y is hydroxyl group, the reaction can be conducted by reacting the compound (III) with 1.0 to 1.5 equivalent, preferably 1.2 equivalent of the compound (IV) in the presence of 1 to 5 equivalent, preferably 1.2 equivalent of the condensing agent such as 1-ethyl-3-(3-dimethyl-aminopropyl)carbodiimide hydrochloride, based on the compound (III), and if necessary in the presence of the catalyst such as 4-dimethylaminopyridine in the inert solvent such as dichloromethane.

After the reaction is completed, the reaction mixture is diluted with an organic solvent, which is nonmiscible solvent with water, and the organic layer is washed sequentially with water and saturated saline solution, then, the solvent is removed to give the purpose compound (II). This compound can be purified by column chromatography, if necessary.

Then, the obtained compound (II) is converted to the compound (IA') by pyrimidine ring formation reaction. This ring formation reaction can be carried out by heating the compound (II) with base such as sodium hydroxide, potassium t-butoxide or potassium carbonate in ethanol/water in the seal tube at 120 to 140° C. Further, the reaction can be carried out in high boiling solvent such as methoxyethanol in the presence of base such as potassium t-butoxide at 120 to 140° C. After the reaction is completed, the reaction mixture is diluted with an organic solvent, which is nonmiscible solvent with water, and the organic layer is washed sequentially with water and saturated saline solution. Then, the compound (IA') can be obtained by removal of the solvent. This compound (IA') can be purified by chromatography or recrystallization, if necessary.

The compound (IA") can be obtained from the obtained compound (IA') by the function group converting reaction with per acid such as m-chloroperbenzoic acid or magnesium mono-peroxyphthalate in chloroform or dichloromethane or chloroform at ° C. to the room temperature.

Further, the compound (IA'".) can be obtained by reacting the compound (IA") with lithium amide, which is obtained by reacting the amine compound with n-butyllithium. For example, to 2 to 5 equivalent of amine compound based on the compound (IA") in ethers such as 1,4-dioxan or tertahydrofuran is added by dripping same equivalent of n-butyl lithium to obtain corresponding lithium amide at –78° C. to 0° C., and then the compound (IA") is added to this mixture of lithium amide solution to obtain the compound (IA'"). After the reaction is completed, water is added to the reaction mixture and the mixture is extracted with an organic solvent, which is nonmiscible solvent with water, and the organic layer is washed sequentially with water and saturated saline solution, then, the solvent is removed to give the purpose compound (IA'").

The carboxylic compound (IV) to be used in the above reaction can be obtained by the following reaction scheme.

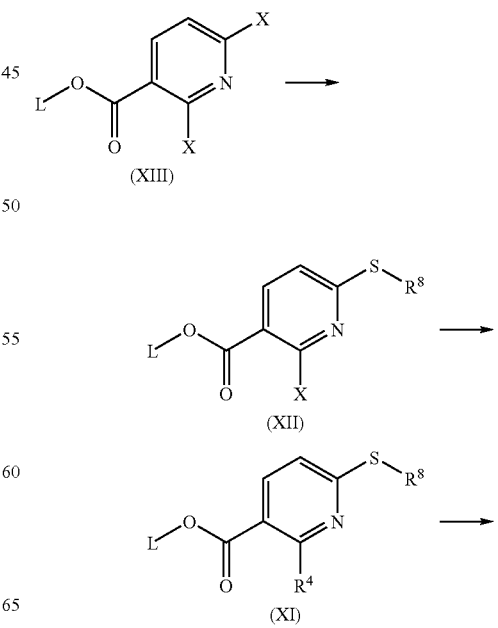

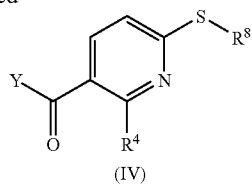

(wherein, L, Y, $R^4$ and $R^6$ have same meaning mentioned above; and X is a halogen atom)

Namely, the compound (XII) is obtained from the compound (XIII) in accordance with the known method (e.g., Chem. Pharm. Bull., 48(12), 1847-1853 (2000)). For example, the reaction can be conducted by reacting the compound (XIII) with about 1 equivalent thiol compound such as ethanethiol or benzenethiol in the presence of base such as potassium t-butoxide, in polar solvent such as N,N-dimethylformamide at the room temperature to −30° C., preferably −30° C. After the reaction is completed, water is added to the reaction mixture and the mixture is extracted with an organic solvent, which is nonmiscible solvent with water, and the organic layer is washed sequentially with water and saturated saline solution. Then, the compound (XII) can be obtained by removal of the solvent. This compound (XII) can be purified by recrystallization, if necessary.

Then, obtained compound (XII) is converted to the compound (XI) in accordance with common method. For example the reaction is conducted by reacting the compound (XII) with small excess of metal alcoholate such as sodium methylate in ethers solvent such as 1,4-dioxan or tetrahydrofuran at the room temperature to refluxing temperature. After the reaction is completed, water is added to the reaction mixture and the mixture is extracted with an organic solvent, which is nonmiscible solvent with water, and the organic layer is washed sequentially with water and saturated saline solution. Then, the compound (XI) can be obtained by removal of the solvent. This compound (XI) can be purified by recrystallization, if necessary.

The obtained compound (XI) is converted to the compound (IV) in accordance with common method. This reaction is hydrolysis reaction of ester compound and various methods are applied. For example the reaction is conducted by reacting the compound (XI) with base such as sodium hydroxide in the alcohol solvent such as methanol or water, as well as a mixture thereof at the room temperature to refluxing temperature. After the reaction is completed, the reaction mixture is condensed and the residue is neutralized to give the compound (IV).

All reaction mentioned above are well known, and the reagents to be used or the reaction conditions to be applied can be easily established in accordance with the standard text book and the examples mentioned later. Further, the other methods or modified methods for obtaining the compound (IA) of the present invention can be easily selected by the person skilled in this field.

The compound of the formula (IB) of the present invention may be synthesized by the following methods.

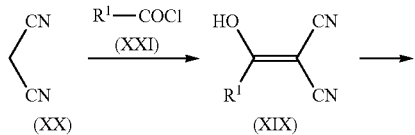

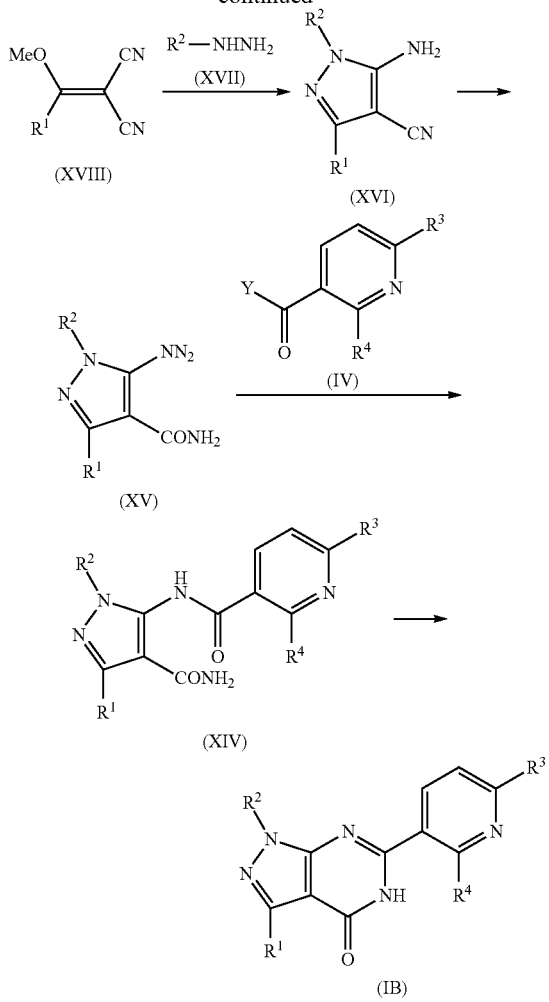

(wherein, $R^1$, $R^2$, $R^3$ and $R^4$ have same meaning mentioned above; and Y is hydroxyl group or halogen atom, preferably chlorine atom)

At the beginning, to carry out the method described above, the compound (XIX) is obtained from the compound (XX) in accordance with the known method (e.g., J. Chem. Soc, Perkin Trans. 1, 1996, 1545-1552). This method can be conducted by the reaction of the compound (XX) with 1 to 1.5 equivalent of the compound (XXI) based on the compound (XX), in the presence of the 2 to 2.5 equivalent of alkali metal hydride such as sodium hydride and potassium hydride, or tertiary amine such as triethlyamine based on the compound (XX). The reaction can be carried out in an appropriate solvent and these are halogenated hydrocarbons such as dichloromethane; aromatic hydrocarbon such as toluene and benzene; ethers solvent such as diethyl ether tetrahydrofuran; or a mixture of solvent thereof. The reaction temperature is a range from 0° C. to the room temperature. After the reaction is completed, the reaction mixture is diluted with an organic solvent, which is nonmiscible solvent with water, and the organic layer is washed sequentially with water and saturated saline solution. Then, the compound (XIX) can be obtained by removal of the solvent. This compound (XIX) can be purified by chromatography, if necessary.

Then, the obtained compound (XIX) is converted to the compound (XVIII) in accordance with the common method (e.g., J. Chem. Soc, Perkin Trans. 1, 1996, 1545-1552). For example, the reaction can be carried out by the reacting the compound (XIX) with 5 to 10 equivalent of the methylation reagent such as dimethyl sulfate in an appropriate solvent. The solvent to be used in this reaction may include halogenated hydrocarbons such as dichloromethane; aromatic hydrocarbon such as toluene and benzene; ethers solvent such as diethyl ether tetrahydrofuran; or a mixture of solvent thereof, and the reaction temperature is from the room temperature to the refluxing temperature of the solvent. After the reaction is completed, the reaction mixture is diluted with an organic solvent, which is nonmiscible solvent with water, and the organic layer is washed sequentially with water and saturated saline solution. Then, the compound (XVIII) can be obtained by removal of the solvent. This compound (XVIII) can be purified by chromatography, if necessary.

Next, the obtained compound (XVIII) is converted to the compound (XVI) in accordance with the common method (e.g., J. Chem. Soc, Perkin Trans. 1, 1996, 1545-1552). For example, the reaction can be carried out by the reacting the compound (XVIII) with 1 to 1.5 equivalent of the compound XVII) based on the compound (XVIII) in an appropriate solvent. The solvent to be used in this reaction may include halogenated hydrocarbons such as dichloromethane; aromatic hydrocarbon such as toluene and benzene; ethers solvent such as diethyl ether tetrahydrofuran; or a mixture solvent thereof, and the reaction temperature is from the room temperature to the refluxing temperature of the solvent. After the reaction is completed, the solvent is removed to give the compound (XVI). This compound (XVI) can be purified by chromatography, if necessary.

Then, the obtained compound (XVI) is converted to the compound (XV) in accordance with the common method. This reaction is hydrolysis reaction of nitrile group converting to the corresponding acid amide group, and various methods are applied. For example, the reaction can be conducted by treating the compound (XVI) with catalyst such as sulfuric acid or hydrochloric acid in an appropriate solvent at the room temperature to 100° C. The solvent to be used is water, alcohols such as methanol or ethanol, ethers such as diethyl ether, tetrahydrofuran or dioxane, or the mixture thereof. After the reaction is completed, the pH of reaction mixture is adjusted to alkali side, and the reaction mixture is extracted with an organic solvent, which is nonmiscible solvent with water, and the organic layer is washed sequentially with water and saturated saline solution. Then, the compound (XV) can be obtained by removal of the solvent. This compound (XV) can be purified by recrystallization, if necessary.

The obtained compound (XV) is, then, converted to the compound (XIV) in accordance with the common method. This reaction can be conducted by the reaction of the compound (XV) with compound (IV) to obtain the corresponding acid amide compound (XIV). For example, in the case of the compound (IV) in which Y is halogen atom, preferably chlorine atom, the reaction can be conducted by reacting the compound (XV) with 1.0 to 2.0 equivalent, preferably about 1.4 equivalent of the compound (IV) in the presence of 1 to 5 equivalent, preferably 2.5 equivalent of tertiary amine such as triethylamine, based on the compound (XV), and if necessary in the presence of the catalyst such as 4-dimethylaminopyridine. The reaction can be carried out in the presence of inert solvent such as dichloromethane at 0° C. to the room temperature.

Furthermore, in the case of the compound (IV) in which Y is hydroxyl group, the reaction can be conducted by reacting the compound (XV) with 1.0 to 1.5 equivalent, preferably about 1.2 equivalent of the compound (IV) in the presence of 1 to 5 equivalent, preferably about 1.2 equivalent of the condensing agent such as 1-ethyl-3-(3-dimethyl-aminopropyl)-carbodiimide hydrochloride, based on the compound (XV), and if necessary in the presence of the catalyst such as 4-dimethylaminopyridine in the inert solvent such as dichloromethane.

After the reaction is completed, the reaction mixture is diluted with an organic solvent, which is nonmiscible solvent with water, and the organic layer is washed sequentially with water and saturated saline solution, then, the solvent is removed to give the purpose compound (XIV).

Then, the obtained compound (XIV) is used for the next reaction without further purification, and is converted to the compound (IB) by pyrimidine ring formation reaction by mean of the known method (e.g., J. Med. Chem., 39 1635-1644(1996)). This ring formation reaction can be carried out by heating the compound (XIV) with base such as sodium hydroxide, potassium t-butoxide or potassium carbonate in ethanol/water in the seal tube at 120 to 140° C. Further, the reaction can be carried out in high boiling solvent such as methoxyethanol in the presence of base such as potassium t-butoxide at 120 to 140° C. After the reaction is completed, the reaction mixture is diluted with an organic solvent, which is nonmiscible solvent with water, and the organic layer is washed sequentially with water and saturated saline solution. Then, the compound (IB) can be obtained by removal of the solvent. This compound (IIB) can be purified by chromatography or recrystallization, if necessary.

All reaction mentioned above are well known, and the reagents to be used or the reaction conditions to be applied can be easily established in accordance with the standard text book and the examples mentioned later. Further, the other methods or modified methods for obtaining the compound (IB) of the present invention can be easily selected by the person skilled in this field.

EXAMPLES

The present invention is illustrated in more detail by way of the following Biological Test and Examples, but it is to be noted that the present invention is not limited by those Examples in any way.

The synthesis of the compounds of the present invention and intermediate compounds to be used in the synthesis are illustrated in the Example mentioned later. Further, the physicochemical data and chemical structure of the compounds and intermediate compounds obtained by the Examples are summarized in the Tables mentions later.

The compound numbers in the Examples are identical to those in the Tables.

The PDE 7 (phosphodiesterase VII) inhibiting effect of the compounds of the present invention obtained in the later mentioned Examples was evaluated by mean of the following Biological Tests.

Biological Test 1:
Methods for Evaluating the PDE 7 Inhibiting Effect

The PDE 7 (phosphodiesterase VII) inhibiting effect of the compounds of the present invention was performed by the following method, which was modified assay method described in *Biochemical. Pharmacol.* 48(6), 1219-1223 (1994).

(1) The active fraction of PDE 7 (phosphodiesterase VII) was obtained. That is, MOLT-4 (obtainable from ATCC as ATCC No. CRL-1582), which was cell line of human acute lymphoblastic lymphoma T cells, was incubated in RPMI1640 culture medium containing 10% fetal bovine serum to obtain $5 \times 10^8$ MOLT-4 cells. The cells were collected by centrifugation and suspended with 10 mL of buffer solution A 125 mM of tris-HCl, 5 mM of 2-mercaptoethnol, 2 mM of benzamidine, 2 mM of EDTA, 0.1 µM of 4-(2-aminoethyl)benzensulfonyl hydrochloride; pH 7.5], then homogenized by Polytron® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2 µm filter to obtain the soluble fraction.

(2) The obtained soluble fraction was filled in equilibrium HiTrap Q column (5 mL×2) with buffer solution A, and phosphodiesterase fractions were eluted by 300 mL of buffer solution A with linear gradient from 0 to 0.8 M NaCl concentration. 5 ml each of 60 eluents were collected, and each eluents were examined for cyclic AMP metabolic activities of phosphodiesterase. The fraction eluting with about 350 mM NaCl concentration parts, where metabolic activities were not inactivated by 10 µM of rolipram (selective inhibitor for phosphodiesterase IV) and 10 µM of milrinone (selective inhibitor for phosphodiesterase III), were collected as storage solution for using to test PDE 7 inhibiting effect.

(3) The tested compound having desired concentration was reacted in the solution of 20 mM tris-HCl (pH 7.5), 1 mM of $MgCl_2$, 100 µM of EDTA, 330 µg/mL of bovine serum albumin, 4 µg/mL of 5'-nucleotidase, 0.1 µCi of $^3$H-cAMP (0.064 µM of cAMP), 10 µM of rolipram in storage solution of PDE 7 for 2 hours at 25° C. After the reaction, suspension of Sephadex®-QAE in 10 mM of HEPES-Na (pH 7.0) was added to the reaction mixture, and the mixture was left at rest for 5 minutes. Further, Sephadex®-QAE was added to the obtained supernatant and the mixture was leaved at rest for 5 minutes, then, the radioactivity of the solution was measured.

(4) $IC_{50}$ was calculated as 50% inhibiting concentration of the metabolic activities of phosphodiesterase VII of the tested compound.

PDE 7 Inhibiting Effect of the Each Tested Compounds:

The following compounds showed no more than 0.1 µM of $IC_{50}$ values. Compounds NO. 16, 17, 18, 20, 21, 22, 25, 26, 27, 28, 29, 32, 33, 36, 37, 43, 44, 47, 48, 49.

Further, the following are PDE 7 inhibiting activities of the tested compounds.:

Compound 26: $IC_{50}$=0.0026 µM;
Compound 32: $IC_{50}$=0.0032 µM;

As described above, the compounds of the present invention showed significant PDE 7 inhibiting effect.

The compounds of the present invention selectively inhibit PDE 7 and their selectivities are more than 10 times compared to PDE 4 (phosphodiesterase IV), which is similar to the PDE 7. Therefore, it is expected that the side effect of the compounds of the present invention caused by PDE 4 to be less. The selectivity against PDE 4 (phosphodiesterase IV) of the compounds of the present invention was affirmed by means of the following Biological Test.

Biological Test 2:

Methods for Evaluating the PDE 4 Inhibiting Effect

The PDE 4 (phosphodiesterase IV) inhibiting effect of the compounds of the present invention was performed by the following method, which was modified assay method described in *Biochemical. Pharmacol.* 48(6), 1219-1223 (1994).

(1) The active fraction of PDE 4 (phosphodiesterase IV) was obtained. That is, the livers obtained from three Balb/c mice (male, 12 weeks: obtainable from CLEA Japan, Inc.) were suspended with 30 mL of buffer solution B [20 mM of bis-tris, 5 mM of 2-mercaptoethnol, 2 mM of benzamidine, 2 mM of EDTA, 0.1 mM of 4-(2-aminoethyl)benzensulfonyl hydrochloride, 50 mM of sodium acetate; pH 6.5], then homogenized by Polytron® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2pm filter to obtain the soluble fraction.

(2) The obtained soluble fraction was filled in equilibrium DEAE sepharose column (1×10cm) with buffer solution B, and phosphodiesterase fractions were eluted by 120 mL of buffer solution B with linear gradient from 0.05 to 1M sodium acetate concentration. 5 ml each of 24 eluents were collected, and each eluents were examined for cyclic AMP metabolic activities of phosphodiesterase. The fraction eluting with about 620 mM of sosdium acetate concentration parts, where metabolic activities were inactivated by 30 µM of rolipram (selective inhibitor for phosphodiesterase IV), were collected as storage solution to test PDE 4 inhibiting effect.

(3) The tested compound having desired concentration was reacted in the solution of 20 mM tris-HCl (pH 7.5), 1 µM of $MgCl_2$, 100 µM of EDTA, 330 µg/mL of bovine serum albumin, 4 µg/mL of 5'-nucleotidase, 0.1 µCi of $^3$H-cAMP (0.064 µM of cAMP), and storage solution of PDE 4 for 2 hours at 25° C. After the reaction, suspension of Sephadex®-QAE in 10 mM of HEPES-Na (pH 7.0) was added to the reaction mixture, and the mixture was left at rest for 5 minutes. Further, Sephadex®-QAE was added to the obtained supernatant and the mixture was left at rest for 5 minutes, then, the radioactivity of the solution was measured.

(4) $IC_{50}$ was calculated as 50% inhibiting concentration of the metabolic activities of phosphodiesterase IV of the tested compound.

As the results of the mentioned above Biological Test 2, the $IC_{50}$ of the compounds of the present invention was more than 10 times weaker than that of PDE 7 inhibiting effect.

The following are PDE 4 inhibiting activities of the tested compounds.

Compound 26: $IC_{50}$=1.2 µM;
Compound 32: $IC_{50}$=0.98 µM;

The compounds of the present invention inhibit PDE 7 selectively, and therefore, enhance cellular cAMP level. Consequently, the compounds of the present invention are useful for treating various kinds of disease such as allergic disease, inflammatory disease or immunologic disease.

For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, GVH disease, and restenosis after angioplasty.

The compounds of the present invention can be used for preparation of the pharmaceutical composition or PDE 7 inhibitor. As an active ingredient, one or more compounds may be administered in the appropriated formulation. The formulation for oral administration may include for example, capsules, granules, fine granules, syrups, dry syrups or the like; the formulation for parenteral administration may include, for example injectable solution, suppository formulation such as rectal suppository or vaginal suppository, nasal administration such as sprays, or percutaneous absorption formulation such as ointment and tapes, and the like.

The administration dose may vary depending on the various kinds of factors. These factors may be the condition of the patients, the severity of the disease, ages, existence of a complication, as well as formulation. A usual recommended daily dose for oral administration is within the range of 0.1-1,000 mg/day/adult, preferably 0.1-500 mg/day/adult, and more preferably 1-100 mg/day/adult. In the case of parenteral administration, a usual recommended daily dose is within the range of 1/1000 to 1/2 based on dose of oral administration. These doses can be adjusted depending on age, as well as the patient's condition.

The toxicological properties of the compounds of the present invention is low, therefore, the compounds of the present invention is expected to have high safety margin.

MANUFACTURING EXAMPLES

The synthesis of the compounds of the present invention is illustrated in the following Examples.

The physicochemical data and chemical structure of the compounds are summarized in the Tables mentions later. The compound numbers in the Examples are identical to those in the Tables.

Example 1

2-Cyclohexyl-5-methyl-2,4-dihydro-3H-pyrazol-3-one

A mixture solution of 14.5 mL (0.134 mol) of methyl acetoacetate and 20.2 g (0.134 mol) of cyclohexylhydrazine hydrochloride was stirred for 2 hours at 120° C., and the mixture was cooled. Then, the reaction mixture was neutralized with 30 mL of 4M-sodium hydroxide solution and extracted with ethyl acetate. The organic layer was washed with water and saturated saline solution and dried over anhydrous sodium sulfate. The solvent was removed under reduced pressure, and the resulting residue was treated with hexane. The resulting precipitate was collected to give 19.0 g (79%) of the titled compound.

Example 2

5-Chloro-1-cyclohexyl-3-methyl-4-nitro-1H-pyrazole

To 9.3 g (51.6 mmol) of the compound obtained by the Example 1 was added 10 mL (107 mmol) of phosphorus oxychloride, and the mixture was stirred for 10 hours at 120° C. The reaction mixture was cooled to the room temperature and excess phosphorus oxychloride was removed off under reduced pressure. The resulting residue was dissolved in 45 mL of acetic anhydride, and to this mixture was gradually added by dripping 9 mL of fuming nitric acid under ice cooling and the mixture was stirred for 2 hours at the same temperature. Then, the mixture was poured into ice and the resulting precipitate was collected and dissolved in dichloromethane. The organic layer was washed with sodium hydrogen carbonate aqueous solution, water and saturated saline solution, and dried over anhydrous sodium sulfate. The solvent was removed under reduced pressure, and the residue was recrystallized from hexane to give 6.28 g (50%) of the title compound. Further, the filtrate was removed off under reduced pressure and the resulting residue was purified by silica gel column chromatography (eluent: hexane/ethyl acetate=6/1) to give 4.21 g (33%) of the title compound.

Example 3

1-Cyclohexyl-3-methyl-4-nitro-1H-pyrazole-5-carbonitrile

To a solution of 10.3 g (42.2 mmol) of the compound obtained in the Example 2 in 90 mL of N,N-dimethylformamide was added 4.2 g (84.9 mmol) of sodium cyanide, and the mixture was stirred for 1.5 hours at 80° C. After the reaction mixture was cooled to the room temperature, the reaction mixture was treated with water and extracted with dichloromethane. The organic layer was washed with water and saturated saline solution, and dried over anhydrous sodium sulfate. The solvent was removed under reduced pressure and the resulting residue was purified by silica gel column chromatography (eluent: hexane/ethyl acetate=6/1) to give 9.18 g (93%) of the title compound.

Example 4

4-Amino-1-cyclohexyl-3-methyl-1H-pyrazole-5-carbonitrile

To a solution of 1.0 g (4.27 mmol) of the compound obtained in the Example 3 in 10 mL of methanol and 10 mL of concentrated hydrochloric acid was added 1.2 g (21.4 mmol) of iron powder, and the mixture was refluxed for 2 hours. Then, the reaction mixture was cooled to the room temperature, neutralized by sodium hydrogen carbonate aqueous solution, and filtrated with Celite®. The filtrate was extracted with dichloromethane, and the organic layer was washed with water and saturated saline solution and dried over anhydrous sodium sulfate. The solvent was removed under reduced pressure and the resulting residue was purified by silica gel column chromatography (eluent: hexane/ethyl acetate=7/1) to give 0.75 g (87%) of the title compound.

Example 5

1-Cyclohexyl-3-methyl-4-nitro-1H-pyrazole-5-carboxamide

To a solution of 9.0 g (38.5 mmol) of the compound obtained in the Example 3 in 25 mL of methanol were added 12 mL of 30% hydrogen peroxide aqueous solution and 30 mL of 3M-sodium hydroxide aqueous solution, and the mixture was stirred at room temperature for 1.5 hours. Then, water was added to the reaction mixture and the mixture was extracted with dichloromethane. The organic layer was washed with water and saturated saline solution, and dried over anhydrous sodium sulfate. The solvent was removed to give 7.8 g (80%) of the title compound.

Example 6

4-Amino-1-cyclohexyl-3-methyl-1H-pyrazole-5-carboxamide

To a suspension of 7.7 g (30.6 mmol) of the compound obtained in the Example 5 in 180 mL of concentrated hydrochloric acid was added 27.6 g (122 mmol) of zinc chloride dihydrate, and the mixture was stirred for 1.5 hours at 80° C. Then, the reaction mixture was cooled to the room temperature and neutralized with sodium hydroxide aqueous solution. After filtrated by Celite®, the filtrate was extracted with dichloromethane, and the organic layer was washed with water and saturated saline solution, and dried over anhydrous sodium sulfate. The solvent was removed under reduced pressure and the residue was purified by silica gel column chromatography (eluent: ethyl acetate) to give 6.05 g (89%) of the title compound.

Example 7

2-Methoxy-6-[(4-methylphenyl)sulfanyl]nicotinic acid

To a suspension of 9.25 g (31.96 mmol) of methyl 2-methoxy-6-(4-methyl benzylthio)pyridine-3-carboxylate in 80 mL of methanol was added 38.36 mL (38.36 mmol) of 1N-sodium hydroxide aqueous solution, and the mixture was refluxed for 1 hour. After the reaction mixture was cooled to the room temperature, the solvent was removed under reduced pressure and the residue was diluted with water. Then 2N-HCl was added to the solution and the resultant precipitate was collected to obtain 8.92 g (quantitative) of the title compound.

Example 8

1-Cyclohexyl-5-{2-methoxy-6-[(4-methylpheny)sulfanyl]-3-pyridinyl}-3-methyl-1,6-dihydro-7H-pyrazolo[4,3-d]pyrimidin-7-one To a suspension of 3.03 g (11 mmol) of the compound obtained in the Example 7 in 30 mL of 1,2-dichloroethane was added 1.60 mL (22 mmol) of thionyl chloride, and the mixture was refluxed for 1.5 hours. After the reaction mixture was cooled to the room temperature, the solvent was removed under reduced pressure to give the corresponding acid chloride.

To a solution of 2.22 g (10 mmol) of the compound obtained in the Example 6 in 30 mL of chloroform were added above acid chloride in 20 mL of chloroform, 3.48 mL (25 mmol) of triethylamine and 5 mg of dimethyl-aminopyridine, and the mixture was stirred over night. Then, water was added to the reaction mixture and the mixture was extracted with chloroform. The organic layer was washed with saturated saline solution and dried over anhydrous sodium sulfate. The solvent was removed under reduced pressure to give the corresponding amide compound as pale yellowish solid.

The obtained amide compound was suspended in 50 mL of methoxyethanol and to this mixture was added 2.81 g (25 mmol) of potassium tert-butoxide and the mixture was stirred for 40 minutes at 130° C. After the reaction mixture was cooled to the room temperature, the solvent was removed under reduced pressure. The resulting residue was diluted with water and 26 mL of 1N-HCl was added. The mixture was extracted with chloroform and the organic layer was dried over anhydrous sodium sulfate. The solvent was removed under reduced pressure and the resulting residue was purified by silica gel column chromatography (eluent: hexane/ethyl acetate=3/1) to give 3.64 g (79%) of the title compound.

Example 9

1-Cyclohexyl-5-{2-methoxy-6-[(4-methylphenyl)sulfonyl]-3-pyridinyl}-3-methyl-1,6-dihydro-7H-pyrazolo[4,3-d]pyrimidin-7-one To a solution of 1.5 g (3.25 mmol) of the compound obtained in the Example 8 in 40 mL of dichloromethane was added 1.54 g (7.15 mmol) of m-chloro-perbenzoic acid at 0° C., and the mixture was stirred for 2 hours. Then, saturated sodium hydrogen carbonate aqueous solution was added to the mixture and the mixture was extracted with dichloromethane. The organic layer was dried over anhydrous sodium sulfate and the solvent was removed under reduced pressure to give 1.75 g (quantitative) of the title compound. This compound was used for the next reaction without further purification.

Example 10

2-[Cyclohexyl(hydroxyl)methylene]malononitrile

To a solution of 3.96 g (0.06 mol) of malononitrile in 60 mL of tetrahydrofuran was added 4.8 g (60% dispersion in mineral oil; 0.12 mol) of sodium hydride in 4 separate times at 0° C., and the mixture was stirred for 30 minutes at the same temperature. Then, to this mixture was added by dripping cyclohexanecarboxylic chloride and the mixture was stirred for 30 minutes at room temperature. 150 mL of 1M-HCl was added slowly to the reaction mixture and the mixture was extracted with ethyl acetate. The organic layer was dried over anhydrous sodium sulfate and the solvent was removed under reduces pressure. The resulting residue was recrystallized from diisopropyl ether to give 8.16 g (77%) of the title compound.

Example 11

2-[Cyclohexyl(methoxy)methylene]malononitrile

To a mixture of 2.64 g (15 mmol) of the compound obtained in the Example 10 in 24 mL of 1,4-dioxane and 4 mL of water was added 10 g of sodium hydrogen carbonate and 10 mL of dimethyl sulfate was added by dripping for 5 minutes to this mixture. After the mixture was heated for 2.5 hours at 85° C., the reaction mixture was cooled to the room temperature and water was added to the reaction mixture. The mixture was extracted with diethyl ether and the extract was dried over anhydrous sodium sulfate. The solvent was removed under reduced pressure and the resulting residue was purified by silica gel column chromatography (eluent: hexane/ethyl acetate=3/1) to give 2.35 g (82%) of the title compound.

Example 12-1

5-Amino-3-cyclohexyl-1-methyl-1H-pyrazole-4-carbonitrile

To a solution of 2.3 g (12.1 mmol) of the compound obtained in the Example 11 in 20 mL of ethanol was added 0.643 mL (12.1 mmol) of methylhydrazine, and the mixture was refluxed for 5 hours. After the mixture was cooled to the room temperature, the solvent was removed under reduced pressure. The resulting residue was purified by silica gel column chromatography (eluent: dichloromethane/methanol=50/1) to give 1.48 g (60%) of the title compound.

Example 12-2

5-Amino-3-cyclohexyl-1-methyl-1H-pyrazole-4-carbonitrile

To a solution of 17.2 g (260 mmol) of malononitrile in 260 mL of tetrahydrofuran was added slowly to 20.8 g (60% dispersion in mineral oil; 520 mmol) of sodium hydride at 0° C., then, to this mixture was added by dripping 35 mL (260 mmol) of cyclohexanecarbonyl chloride at the same temperature and the mixture was stirred for 1.5 hours at room temperature. Then, 30 mL (312 mmol) of dimethyl sulfate was added to the reaction mixture and the mixture was refluxed for 3 hours. Then, 17.4 mL (125 mmol) of triethylamine and 13.8 mL (260 mmol) of methylhydrazine were added to the reaction mixture under ice cooling and the mixture was refluxed for 1 hour. After the mixture was cooled to the room temperature, the solvent was removed under reduce pressure. Water was added to the residue and the mixture was extracted with ethyl acetate and the organic layer was washed with water, and saturated saline solution, then, dried over anhydrous sodium sulfate. The solvent was removed under reduced pressure and the resulting residue was purified by silica gel column chromatography (eluent: chloroform/methanol=30/1 to 20/1). The obtained crude crystalline was further purified by recrystallization (hexane-ethyl acetate) to give 20.7 g (39%) of the title compound. The filtrate was further purified by silica gel column chromatography (eluent: hexane/ethyl acetate=2: 1) to give 11.3 g (21%) of the title compound.

Example 13

5-Amino-3-cyclohexyl-1-methyl-1H-pyrazole-4-carboxamide 75 mL of concentrated. HCl was added to 25.3 g (124 mmol) of the compound obtained in the Example 12, and the mixture was stirred for 15 minutes at room temperature and for 1 hour at 60° C. Then, the reaction mixture was poured into ice, neutralized by sodium hydroxide aqueous solution and extracted with dichloromethane. The organic layer was washed with water and saturated saline solution, and dried over anhydrous sodium sulfate. The solvent was removed under reduced pressure and the resulting residue was recrystallized from ethyl acetate to give 20.2 g (73%) of the title compound.

Example 14

3-Cyclohexyl-6-{2-methoxy-6-[(4-methylphenyl)sulfanyl]-3-pyridinyl}-1-methyl-1,5-dihydro-4H-pyrazolo[3,4-d]pyrimidin-4-one To a suspension of 2.70 g (9.81 mmol) of the compound obtained in the Example 7 in 30 mL of 1,2-dichloroethane was added 1.43 mL (19.6 mmol) of thionyl chloride, and the mixture was refluxed for 2 hours. Then, the reaction mixture was cooled to the room temperature and the solvent was removed under reduced pressure to give the corresponding acid chloride as yellowish solid.

To the solution of the obtained acid chloride in 30 mL of pyridine were added 1.82 g (8.17 mmol) of the compound obtained in the Example 13 and 5 mg of dimethylaminopyridine, and the mixture was stirred for 20 hours at room temperature. Then, saturated sodium hydrogen carbonate aqueous solution was added to the reaction mixture and the mixture was extracted with chloroform. The organic layer was washed with water and saturated saline solution, and dried over anhydrous sodium sulfate. The solvent was removed under reduced pressure to give the corresponding amide compound as pale yellowish solid.

The obtained amide compound was suspended in 50 mL of methoxyethanol and to this suspension was added 2.30 g (20.4 mmol) of potassium t-butoxide, then the mixture was stirred for 2 hours at 140° C. After the reaction mixture was cooled to the room temperature, the mixture was condensed under reduced pressure and water was added to the residue. Further added 21 mL of 1N-HCl to the mixture, the mixture was extracted with chloroform. The organic layer was washed with water and saturated saline solution, and dried over anhydrous sodium sulfate. The solvent was removed under reduced pressure and the resulting residue was purified by silica gel column chromatography (eluent: dichloromethane/methanol=100/1), and resultant product was further purified by silica gel column chromatography (eluent: hexane/ethyl acetate=2/1) and recrystallized from ethyl acetate to give 1.12 g (30%) of the title compound.

Example 15

3-Cyclohexyl-6-{2-methoxy-6-[(4-methylphenyl)surfonyl]-3-Pyridinyl}-1-methyl-1,5-dihydro-4H-pyrazolo[3,4-d]pyrimidin-4-one The title compound 1.02 g (87%) was obtained in a manner similar to the Example 9 by using the compound obtained in the Example 14, instead of the compound obtained in the Example 8.

Example 16

1-Cyclohexyl-5-[2-methoxy-6-(4-methyl-1-piperazinyl)-3-pyridinyl]-3-methyl-1,6-dihydro-7H-pyrazolo[4,3-d]pyrimidin-7-one To a solution of 134 µL (1.22 mmol) of N-methylpiperazine in 5 mL of tetrahyrofuran was added by dripping 779 µL of n-butyllithium in hexane solution (1.56M hexane solution: 1.22 mmol) at −30° C., and the mixture was stirred for 15 minutes at the same temperature. Then, to this mixture was added the compound obtained in the Example 9 at −30° C., and the mixture was stirred for 15 minutes. After adding water to the mixture and the temperature of the reaction mixture was raised to the room temperature, and the mixture was extracted with ethyl acetate. The organic layer was dried over anhydrous sodium sulfate, and the solvent was removed under reduced pressure. The resulting residue was purified by silica gel column chromatography (eluent: dichloromethane/methanol=30/1) to give 123 mg (93%) of the title compound.

Example 17

1-Cyclohexyl-5-[2-methoxy-6-(4-morpholinyl)-3-pyridinyl]-3-methyl-1,6-dihydro-7H-pyrazolo[4,3-d]pyrimidin-7-one The title compound 72 mg (56%) was obtained in a manner similar to the Example 16 using morpholine, instead of N-methylpiperazine.

Example 18

1-Cyclohexyl-5-[2-methoxy-6-(4-methyl-1,4-diazepan-1-yl)-3-pyridinyl]-3-meth-1-1,6-dihydro-7H-pyrazolo[4,3-d]pyrimidin-7-one The title compound 16 mg (12%) was obtained in a manner similar to the Example 16 by using N-methyl-homopiperazine, instead of N-methylpiperazine.

Example 19

1-Cyclohex-yl-5-(2-methoxy-3-pyridinyl)-3-methyl-1,6-dihydro-7H-pyrazolo[4,3-d]pyrimidin-7-one To a solution of 200 mg (0.90 mmol) of the compound obtained in the Example 6 in 3 mL of dichloromethane were added to 165 mg (1.08 mmol) of 2-methoxynicotinic acid and 207 mg (1.08 mmol) of 1-ethyl-3-(3-dimethyl-aminopropyl)carbodiimide hydrochloride, and the mixture was stirred for over night at room temperature. After adding saturated sodium hydrogen carbonate aqueous solution, the mixture was extracted with dichloromethane. The organic layer was washed with water and saturated saline solution, and dried over anhydrous sodium sulfate. The solvent was removed under reduced pressure, then, 6 mL of ethanol and 3 mL of sodium hydroxide aqueous solution were added to the residue, and the mixture was refluxed for 9 hours. After the reaction mixture was cooled to the room temperature, water was added and the mixture was extracted with dichloromethane. The organic layer was washed with water and saturated saline solution, and dried over anhydrous sodium sulfate. The solvent was removed under reduced pressure, and the resulting residue was purified by silica gel column chromatography (eluent: hexane/ethyl acetate=2/1). The obtained product was recrystallized from the mixture solvent of ethyl acetate-hexane to give 78 mg (26%) of the title compound.

Example 20

3-Cyclohexyl-6-[2-methoxy-6-(4-methyl-1-piperazinyl)-3-pyridinyl]-1-methyl-1,5-dihydro-4H-pyrazolo[3,4-d]pyrimidin-4-one The title compound 86 mg (65%) was obtained in a manner similar to the Example 16 using the compound obtained in the Example 15, instead of the compound obtained in the Example 9.

Example 21

3-Cyclohexyl-6-[2-methoxy-6-(4-morpholinyl)-3-pyridinyl]-1-methyl-1,5-dihydro-4H-pyrazolo[3,4-d]pyrimidin-4-one The title compound 58 mg (45%) was obtained in a manner similar to the Example 16 using morpholine and the compound obtained in the Example 15, instead of N-methylpiperazine and the compound obtained in the Example 9, respectively.

Example 22

3-Cyclohexyl-6-[2-methoxy-6-(4-methyl-1,4-diazepan-1-yl)-3-pyridinyl]-1-methyl-1.5-dihydro-4H-pyrazolo[3,4-d]pyrimidin-4-one The title compound 115 mg (84%) was obtained in a manner similar to the Example 16 using N-methyl-homopirerazine and the compound obtained in the Example 15, instead of N-methylpiperazine and the compound obtained in the Example 9, respectively.

Example 23

3-Cyclohexyl-6-[6-(1,4-dioxa-8-azaspiro[4,5]dec-8-yl)-2-methoxy-3-pyridinyl]-1-methyl-1,5-dihydro-4H-pyrazolo[3,4-d]pyrimidin-4-one The title compound 776 mg (quantitative) was obtained in a manner similar to the Example 16 using 1,4-dioxa-8-azaspiro[4.5]decane and the compound obtained in the Example 15, instead of N-methylpiperazine and the compound obtained in the Example 9, respectively.

Example 24

3-Cyclohexyl-6-[2-methoxy-6-(4-oxo-1-piperidinyl)-3-pyridinyl]-1-methyl-1,5-dihydro-4H-pyrazolo[3,4-d]pyrimidin-4-one To a suspension of 743 mg (1.55 mmol) of the compound obtained in the Example 23 in 30 mL of acetone and 3 mL of water was added 353 mg (1.86 mmol) of p-toluenesulfonic acid hydrate, and the mixture was refluxed for 5 hours. After the reaction mixture was cooled to the room temperature, the solvent was removed under reduced pressure, saturated sodium hydrogen carbonate aqueous solution was added to the reaction mixture and the mixture was extracted with dichloromethane. The organic layer was washed with saturated saline solution and dried over anhydrous sodium sulfate. The solvent was removed under reduced pressure and the residue was recrystallized from mixture solvent of ethyl acetate-ethanol to give 405 mg (93%) of the title compound.

Example 25

3-Cyclohexyl-6-[6-(4-hydroxy-1-piperidinyl)-2-methoxy-3-pyridinyl]-1-methyl-1,5-dihydro-4H-pyrazolo[3,4-d]pyrimidin-4-one To a suspension of 120 mg (0.28 mmol) of the compound obtained in the Example 24 in 3 mL of methanol was added 12.5 mg (0.33 mmol) of sodium borohydride, and the mixture was stirred for 2.5 hours at room temperature. Then, acetone was added to the reaction mixture and the solvent was removed under reduced pressure. Water was added to the residue and the mixture was extracted with dichloromethane. The organic layer was washed with water and saturated saline solution and dried over anhydrous sodium sulfate. The solvent was removed under reduced pressure and the resulting residue was purified by silica gel column chromatography (eluent: dichloromethane/ethyl acetate=2/1 to 1/2), and the obtained crude product was recrystallized from ethanol to give 85 mg (70%) of the title compound.

Example 26

3-Cyclohexyl-6-{2-methoxy-6-[4-(methylamino)-1-piperidinyl]-3-pyridinyl}-1-methyl-1,5-dihydro-4H-pyrazolo[3,4-d]-pyrimidin-4-one To a suspension of 120 mg (0.28 mmol) of the compound obtained in the Example 24 in 2 mL of 1,2-dichloromethane were added to 57 μM (30% ethanol solution; 0.55 mmol) of methylamine, 10M of acetic acid and 87 mg (0.41 mmol) of sodium triacetoxyborohydride, and the mixture was stirred for 2 hours at room temperature. Then, saturated sodium hydrogen carbonate aqueous solution was added to the reaction mixture and the mixture was extracted with dichloromethane. The organic layer was washed with water and saturated saline solution and dried over anhydrous sodium sulfate. The solvent was removed under reduced pressure and the resulting residue was purified by silica gel column chromatography (eluent: dichloromethane/ethyl acetate/methanol=10/10/1). The obtained crude product was recrystallized from the mixture solvent of ethyl acetate-hexane to give 87 mg (70%) of the title compound.

Example 27

3-Cyclohexyl-6-{6-[4-(dimethylamino)-1-piperidinyl]-2-methoxy-3-pyridinyl}-1-methyl-1,5-dihydro-4H-pyrazolo[3,4-d]-pyrimidin-4-one The title compound 103 mg (80%) was obtained in a manner similar to the Example 26 using dimethylamine, instead of methylamine.

Example 28

6-[6-(4-Amino-1-piperidinyl)-2-methoxy-3-pyridinyl]-3-cyclohexyl-1-methyl-1,5-dihydro-4H-pyrazolo[3,4-d]pyrimidin-4-one To a mixture of 240 mg (0.55 mmol) of the compound obtained in the Example 24 in 10 mL of 4M-ammnonia-etanol solution was added 24 mg of 5% palladium-carbon and the mixture was stirred for 24 hours under hydrogen gas atmosphere at normal pressures. After the reaction, the mixture was filtrated by Celite® and filtrate was removed under reduced pressure. The resulting residue was purified by alkaline silica gel column chromatography (eluent: dichloromethane/ethyl acetate/methanol=10/10/1) and obtained crude product was recrystallized from ethanol to give 169 mg (70%) of the title compound.

Example 29

N-{1-[5-(3-Cyclohexyl-1-methyl-4-oxo-4,5-dihydro-1H-pyrazolo[3,4-d]-pyrimidin-6-yl)-6-methoxy-2-piridinyl]-4-piperidinyl}acetamide To a solution of 80 mg (0.18 mmol) of the compound obtained in the Example 28 in 2 mL of dichloromethane were added 21 µL (0.22 mmol) of acetic anhydride and 38 µL of triethylamine, and the mixture was stirred for 1.5 hours at room temperature. Then, saturated sodium hydrogen carbonate aqueous solution was added to the reaction mixture and the mixture was extracted with dichloromethane. The organic layer was washed with water and saturated saline solution and dried over anhydrous sodium sulfate. The solvent was removed under reduced pressure and the residue was recrystallized from ethanol to give 79 mg (90%) of the title compound.

Example 30

1-Cyclohexl-5-[6-(1,4-dioxa-8-axaspiro[4.5]dec-8-yl)-2-methoxy-3-pyridinyl]-3-methyl-1,6-dihydro-7H-pyrazolo[4,3-d]pyrimidin-7-one The title compound 588 mg (86%) was obtained in a manner similar to the Example 16 using 1,4-dioxa-8-axaspiro[4.5]decane instead of N-methylpiperazine.

Example 31

1-Cyclohexyl-5-[2-methoxy-6-(4-oxo-1-piperidinyl)-3-pyridinyl]-3-methyl-1,6-dihydro-7H-pyrazolo[4,3-d]-pyrimidin-7-one The title compound 255 mg (50%) was obtained in a manner similar to the Example 24 using the compound obtained in the Example 30 instead of the compound obtained in the Example 23.

Example 32

1-Cyclohexyl-5-{2-methoxy-6-[(4-(methylamino)-1-piperidinyl)-3-pyridinyl}-3-methyl-1,6-dihydro-7H-pyrazolo[4,3-d]-pyrimidin-7-one The title compound 68 mg (55%) was obtained in a manner similar to the Example 26 using the compound obtained in the Example 31 instead of the compound obtained in the Example 24.

Example 33

1-Cyclohexyl-5-{-6-[4-(dimethylamino)-1-piperidinyl]-2-methoxy-3-pyridinyl]-3-methyl-1,6-dihydro-7H-pyrazolo4,3-d]-pyrimidin-7-one The title compound 102 mg (94%) was obtained in a manner similar to the Example 26 using the compound obtained in the Example 31 and dimethylamine instead of the compound obtained in the Example 24 and methylamine, respectively.

Example 34

3-Cyclohexyl-6-(2-methoxy-6-sulfanyl-3-piridinyl)-1-methyl-1,5-dihydro-4H-pyrazolo[3,4-d]-pyrimidin-4-one To a suspension of 230 mg (0.47 mmol) of the compound obtained in the Example 15 in 5 mL of methanol was added 100 mg of sodium hydrosulfide, and the mixture was refluxed for 4 hours. After cooling, 1M-HCl was added to the reaction mixture and the precipitate was collected. The obtained solid was purified by silica gel column chromatography (eluent: dichloromethane/methanol=20/1) to give 132 mg (76%) of the title compound.

Example 35

5-(3-Cyclohexyl-1-methyl-4-oxo-4,5-dihydro-1H-pyrazolo-[3,4-d]pyrimidin-6-yl)-6-methoxy-2-pyridinesulfonyl chloride To a suspension of 120 mg (0.32 mmol) of the compound obtained in the Example 34 in 3 mL of acetonitrile was added 82 mg (0.81 mmol) of potassium nitrate and to this mixture was added 65 µL (0.81 mmol) of sulfuryl chloride at 0° C. The mixture was stirred for 2 hours at room temperature, then, water was added to the reaction mixture. The precipitate was collected to give 114 mg (81%) of the title compound.

Example 36

3-Cyclohexyl-6-{2-methoxy-6-[(4-methyl-1,4-diazepan-1-yl)sulfonyl]-3-pyridinyl}-1-methyl-1,5-dihydro-4H-pyrazolo[3,4-d]pyrimidin-4-one To a solution of 104 mg (0.24 mmol) of the compound obtained in the Example 35 in 2 mL of dichloromethane were added 35 µL (0.29 mmol) of N-methyl-homopiperazine and 83 µL (0.59 mmol) of triethylamine, and the mixture was stirred for 1 hour at room temperature. Then, saturated sodium hydrogen carbonate aqueous solution was added to the reaction mixture and the mixture was extracted with dichloromethane. The organic layer was washed with water and saturated saline solution, and dried over anhydrous sodium sulfate. The solvent was removed under reduced pressure and the resulting residue was purified by alkaline silica gel column chromatography (eluent: ethyl acetate). The obtained crude solid was recrystallized from ethyl acetate-hexane to give 68 mg (56%) of the title compound.

Example 37

1-Cyclohexyl-5-[6-(4-hydroxy-1-piperidinyl)-2-methoxy-3-pyridinyl]-3-methyl-1,6-dihydro-7H-pyrazolo[4,3-d]pyrimidin-7-one The title compound 73 mg (60%) was obtained in a manner similar to the Example 25 using the compound obtained in the Example 31 instead of the compound obtained in the Example 24.

Example 38

1-Cyclohexyl-5-{2-methoxy-6-[(4-methylphenyl)sulfinyl]-3-pyridinyl}-3-methyl-1,6-dihydro-7H-pyrazolo[4,3-d]pyrimidin-7-one To a solution of 1.5 g (3.25 mmol) of the compound obtained in the Example 8 in 30 mL of dichloromethane was added 701 mg (3.25 mmol) of m-chloroperbenzoic acid at 0° C., and the mixture was stirred for 40 minutes. Then, saturated sodium hydrogen carbonate aqueous solution was added to the reaction mixture and the mixture was extracted with dichloromethane. After the solvent was dried over anhydrous sodium sulfate, the solvent was removed under reduced pressure. The residue was recrystallized from 2-butanone to give 1.0 g (64%) of the title compound.

Example 39

Ethyl 2-ethoxy-6-[(4-methylphenyl)sulfanyl]nicotinate

To a solution of 11.5 g (92.4 mmol) in 55 mL of N,N-dimethylformamide was added 10.8 g (96.0 mmol) of potassium tert-butoxide at 0° C., and the mixture was stirred for 15 minutes at room temperature. This mixture was added by dripping to a solution of 19.56 g (88.9 mmol) of ethyl 2,6-dichloronicotinate in 150 mL of N,N-dimethylformamide at −30° C. for 15 minutes, and the mixture was stirred for 1 hour at the same temperature. Then, the reaction mixture was poured into ice water and extracted with a mixture solution of ethyl acetate/hexane (2/1). The organic layer was washed with water and saturated saline solution, then, dried over anhydrous sodium sulfate. The solvent was removed under reduced pressure to give ethyl 2-chloro-6-[(4-methylphenyl)sulfanyl]nicotinate intermediate as pale brown oil.

Then, this compound was dissolved in 180 mL of tetrahydrofuran and 31.4 g (92.4 mmol) of 20% sodium ethoxide-ethanol solution was added to this solution, and the mixture was refluxed for 2 hours. After the reaction mixture was cooled to the room temperature, the mixture was filtered, and the filtrate was removed under reduced pressure. The residue was diluted with chloroform and the organic layer was washed with water and saturated saline solution, then, dried over anhydrous sodium sulfate. The solvent was removed under reduced pressure and the residue was purified by silica gel column chromatography (eluent: hexane/ethyl acetate=5/1) to give 23.4 g (83%) of the title compound.

Example 40

2-Ethoxy-6-[(4-methylphenyl)sulfanyl]nicotinic acid

The title compound 20.16 g (97%) was obtained in a manner similar to the Example 7 using the compound obtained in the Example 39 instead of methyl 2-methoxy-6-(4-methylbenzylthio)pyridine-3-carboxylate.

Example 41

1-Cyclohexyl-5-{2-ethoxy-6-[(4-methylphenyl)sulfanyl]-3-pyridinyl}-3-methyl-1,6-dihydro-7H-pyrazolo[4,3-d]pyrimidin-7-one To a suspension of 3.18 g (11 mmol) of the compound obtained in the Example 40 in 30 mL of 1,2-dichloromethane was added 1.60 mL of thionyl chloride, and the mixture was refluxed for 2 hours. Then, the reaction mixture was cooled to the room temperature and the solvent was removed under reduced pressure to give the corresponding acid chloride as pale yellow solid. Then, this acid chloride was dissolved in 30 mL of dichloromethane and to this solution were added 3.48 mL (25 mmol) of triethylamine, 2.22 g (10 mmol) of the compound obtained in the Example 6, and 50 mL of dichloromethane, and then, the mixture was stirred for 2 hours at room temperature. Saturated sodium hydrogen carbonate aqueous solution was added the reaction mixture and the mixture was extracted with chloroform. The organic layer was washed with water and saturates saline solution, dried over anhydrous sodium sulfate, and removed under reduced pressure to give the corresponding amide compound as intermediate. Then, this amide compound was suspended in 100 mL of ethanol and to this suspension was added 2.81 g (25 mmol) of potassium tert-butoxide, and the mixture was refluxed for 14 hours. After the reaction mixture was cooled to the room temperature, the solvent was removed under reduced pressure. The residue was diluted with water and 20 mL of 2N-HCl was added, and extracted with dichloromethane. The organic layer was washed with water and saturated saline solution, and dried over anhydrous sodium sulfate. The solvent was removed under reduced pressure and the residue was purified by silica gel column chromatography (eluent: dichloromethane/ hexane/ethyl acetate=10/20/1 to 10/10/1) to give 3.48 g (73%) of the title compound.

Example 42

1-Cyclohexyl-5-{2-ethoxy-6-[(4-methylphenyl)sulfonyl]-3-pyridinyl}-3-methyl-1,6-dihydro-7H-pyrazolo[4,3-d]pyrimidin-7-one The title compound 2.97 g (93%) was obtained in a manner similar to the Example 9 using the compound obtained in the Example 41 instead of the compound obtained in the Example 8.

Example 43

1-Cyclohexyl-5-[2-ethoxy-6-[(4-methyl-piperazinyl)-3-pyridinyl]-3-methyl-1,6-dihydro-7H-pyrazolo[4,3-d]pyrimidin-7-one The title compound 131 mg (98%) was obtained in a manner similar to the Example 16 using the compound obtained in the Example 42 instead of the compound obtained in the Example 9.

Example 44

1-Cyclohexyl-5-[2-ethoxy-6-(4-methyl-1,4-diazepan-1-yl)-3-pyridinyl]-3-methyl-1,6-dihydro-7H-pyrazolo[4,3-d]pyrimidin-7-one The title compound 128 mg (93%) was obtained in a manner similar to the Example 16 using N-methylhomopiperazine and the compound obtained in the Example 42, instead of N-methylpiperazine and the compound obtained in the Example 9, respectively.

Example 45

1-Cyclohexyl-5-[6-(1,4-dioxa-8-azaspiro[4.5]dec-8-yl)-2-ethoxy-3-pyvridinyl]-3-methyl-1,6-dihydro-7H-pyrazolo[4,3-d]pyrimidin-7-one The title compound 934 mg (96%) was obtained in a manner similar to the Example 16 using 1,4-dioxa-8-azaspiro[4,5]decane and the compound obtained in the Example 42, instead of N-methylpiperazine and the compound obtained in the Example 9, respectively.

Example 46

1-Cyclohexyl-5-[2-ethoxy-6-(4-oxo-1-piperidinyl)-3-pyridinyl]-3-methyl-1,6-dihydro-7H-pyrazolo[4,3-d]pyrimidin-7-one The title compound 791 mg (97%) was obtained in a manner similar to the Example 24 using the compound obtained in the Example 45 instead of the compound obtained in the Example 23.

Example 47

1-Cyclohexyl-5-{6-[4-(dimethylamino)-1-piperidinyl]-2-ethoxy-3-pyridinyl}-3-methyl-1,6-dihydro-7H-pyrazolo[4,3-d]pyrimidin-7-one The title compound 122 mg (86%) was obtained in a manner similar to the Example 26 using dimethylamine and the compound obtained in the Example 46, instead of methylamine and the compound obtained in the Example 24, respectively.

Example 48

1-Cyclohexyl-5-{2-ethoxy-6-[4-(methylamino)-1-piperidinyl]-3-pyridinyl}-3-methyl-1,6-dihydro-7H-pyrazolo[4,3-d]pyrimidin-7-one The title compound 103 mg (83%) was obtained in a manner similar to the Example 26 by using the compound obtained in the Example 46 instead of the compound obtained in the Example 24.

Example 49

1-Cyclohexyl-5-[2-ethoxy-6-(4-hydroxy-1-piperidinyl)-3-pyridinyl]-3-methyl-1,6-dihydro-7H-pyrazolo[4,3-d]pyrimidin-7-one The title compound 92 mg (76%) was obtained in a manner similar to the Example 25 using the compound obtained in the Example 46 instead of the compound obtained in the Example 24.

Physicochemical data of the compounds obtained by the above-mentioned examples are summarized in the following Tables.

TABLE 1

| Example No. | Chemical Structure | Properties m.p.(° C.) (recryst. solvent) | $^1$H-NMR | MS(FAB) $(M + 1)^+$ |
|---|---|---|---|---|
| 1 | 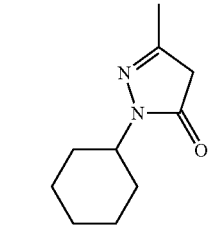 | colorless solid 147.6-150.4 | CDCl$_3$ 1.21-1.36(1H, m), 1.39-1.52(2H, m), 1.71-1.98(7H, m), 2.09(3H, s), 3.20(2H, s), 3.95-4.02(1H, m) | 181 |
| 2 | 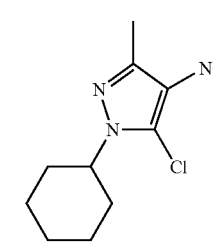 | colorless solid 104.8-105.2 (hexane) | CDCl$_3$ 1.22-1.50(3H, m), 1.70-1.79(1H, m), 1.88-2.01 (6H, m), 2.54(3H, s), 4.23-4.33(1H, m) | 244 |

TABLE 1-continued

| Example No. | Chemical Structure | Properties m.p.(° C.) (recryst. solvent) | ¹H-NMR | MS(FAB) (M + 1)⁺ |
|---|---|---|---|---|
| 3 | (pyrazole with NO₂, CH₃, CN, N-cyclohexyl) | colorless solid 109.0-110.2 (hexane/AcOEt) | CDCl₃ 1.22-1.37(1H, m), 1.39-1.54(2H, m), 1.72-1.82(1H, m), 1.91-2.10(6H, m), 2.58(3H, s), 4.32-4.43(1H, m) | 235 |
| 4 | (pyrazole with NH₂, CH₃, CN, N-cyclohexyl) | pale yellow solid 85.5-87.0 (hexane) | CDCl₃ 1.18-1.31(1H, m), 1.32-1.48(2H, m), 1.66-1.75(1H, m), 1.79-2.03(6H, m), 2.16(3H, s), 3.33(2H, brs), 4.02-4.14(1H, m) | 205 |

TABLE 2

| Example No. | Chemical Structure | Properties m.p.(° C.) (recryst. solvent) | ¹H-NMR | MS (FAB) (M + 1)⁺ |
|---|---|---|---|---|
| 5 | (pyrazole with NO₂, CH₃, CONH₂, N-cyclohexyl) | colorless solid 148.1-149.0 (AcOEt/hexane) | CDCl₃ 1.19-1.48(3H, m), 1.64-1.77(1H, m), 1.84-2.07(6H, m), 2.52(3H, s), 4.41-4.54(1H, m), 6.04(1H, brs), 6.77(1H, brs) | 253 |
| 6 | (pyrazole with NH₂, CH₃, CONH₂, N-cyclohexyl) | colorless solid 193-194 (AcOEt) | CDCl₃ 1.18-1.31(1H, m),1.38-1.52(2H, m), 1.63-1.74(1H, m), 1.79-2.01(6H, m), 2.21(3H, s), 2.80 (2H, s), 5.18-5.29(1H, m) | 223 |
| 7 | (6-(4-methylphenylthio)-2-methoxypyridine-3-carboxylic acid) | colorless solid 174-175 | CDCl₃ 2.41 (3H, s), 4.03(3H, s), 6.58(1H, d, J=8.1 Hz), 7.26-7.31 (2H, m), 7.46-7.51 (2H, m), 8.14(1H, d, J=8.1 Hz) | 276 |

TABLE 2-continued

| Example No. | Chemical Structure | Properties m.p.(° C.) (recryst. solvent) | ¹H-NMR | MS (FAB) (M + 1)⁺ |
|---|---|---|---|---|
| 8 | 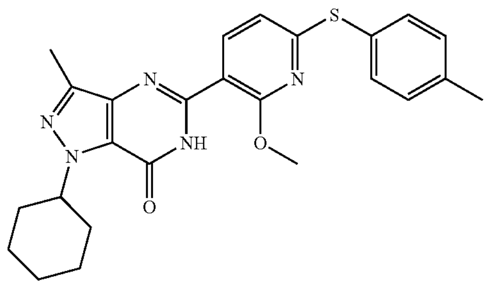 | colorless solid 165-168 | CDCl₃ 1.21-1.35(1H, m), 1.40-1.52(2H, m), 1.65-1.74(1H, m), 1.83-2.06(6H, m), 2.41(3H, s), 2.47 (3H, s), 4.02(3H, s), 4.95-5.05(1H, m), 6.64(1H, d, J=8.3 Hz), 7.23-7.27(2H, m), 7.47-7.51(2H, m), 8.56(1H, d, J=8.3 Hz), 10.72(1H, brs) | 462 |

TABLE 3

| Example No. | Chemical Structure | Properties m.p.(° C.) (recryst. solvent) | ¹H-NMR | MS (FAB) (M + 1)⁺ |
|---|---|---|---|---|
| 9 | 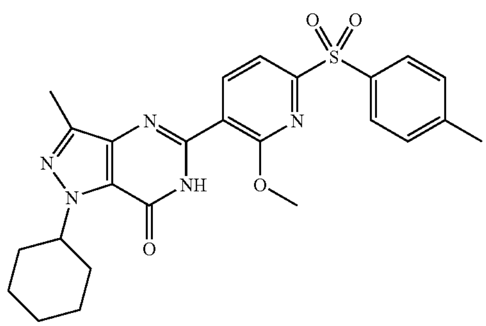 | colorless solid 213-215 | CDCl₃ 1.21-1.34(1H, m), 1.40-1.53(2H, m), 1.67-1.75(1H, m), 1.83-2.06(6H, m), 2.43(3H, s), 2.53 (3H, s), 4.11 (3H, s), 4.95-5.05(1H, m), 7.31-7.36 (2H, m), 7.91-7.97(3H, m), 8.99(1H, d, J=8.0 Hz), 10.63(1H, brs) | 494 |
| 10 | 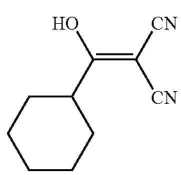 | pale yellow solid 124-129 (di-isopropyl ethr) | CDCl₃ 1.12-1.41(3H, m), 1.45-1.58(2H, m), 1.68-1.89(5H, m), 2.77-2.86(1H, m) | 177 |
| 11 | 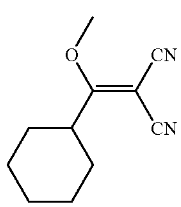 | pale yellow solid 58-59 | CDCl₃ 1.12-1.51 (5H, m), 1.66-1.85(5H, m), 2.77-2.86(1H, m), 4.34(1H, s) | 191 |
| 12 | 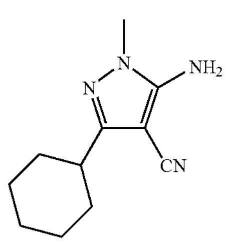 | colorless solid 139-141 | CDCl₃ 1.20-1.41 (3H, m), 1.48-1.62(2H, m), 1.65-1.73(1H, m), 1.77-1.85(2H, m), 1.88-1.97(2H, m), 2.57-2.66(1H, m), 3.58(3H, s), 4.13(2H, br-s) | 205 |

TABLE 4

| Example No. | Chemical Structure | Properties m.p.(° C.) (recryst. solvent) | ¹H-NMR | MS(FAB) (M + 1)⁺ |
|---|---|---|---|---|
| 13 | 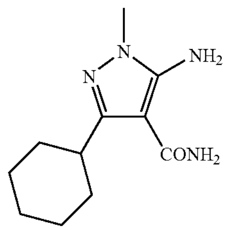 | colorless solid 172-173.5 | CDCl₃ 1.20-1.40(3H, m), 1.52-1.66(2H, m), 1.71-1.78(1H, m), 1.83-1.92(2H, m), 1.98-2.06(2H, m), 2.54-2.63(1H, m), 3.56(3H, s), 5.30(2H, br-s), 5.41 (2H, br-s) | 223 |
| 14 | 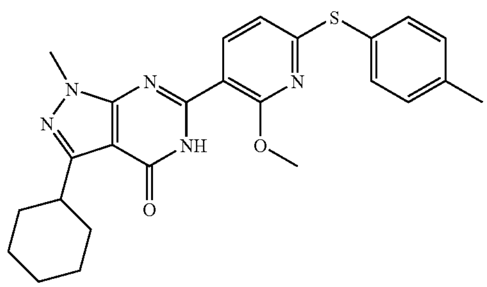 | colorless solid 181-183 (AcOEt) | CDCl₃ 1.27-1.49(3H, m), 1.67-1.87(5H, m), 1.94-2.02(2H, m), 2.41(3H,s), 3.01-3.12(1H, m), 3.90(3H, s), 4.02(3H, s), 6.65(1H, d, J=8.2 Hz), 7.22-7.29(2H, m), 7.47-7.53(2H, m), 8.58(1H, d, J=8.2 Hz), 10.62(1H, brs) | 462 |
| 15 | 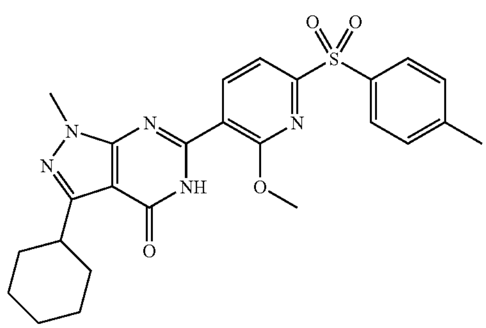 | colorless solid 215-216.5 | CDCl₃ 1.22-1.50(3H, m), 1.66-1.88(5H, m), 1.93-2.04(2H, m), 2.44(3H, s), 3.01-3.11(1H, m), 3.97(3H, s), 4.11(3H, s), 7.31-7.39(2H, m), 7.91-8.00(3H, m), 9.41 (1H, d, J=7.9 Hz), 10.50(1H, brs) | 494 |
| 16 | 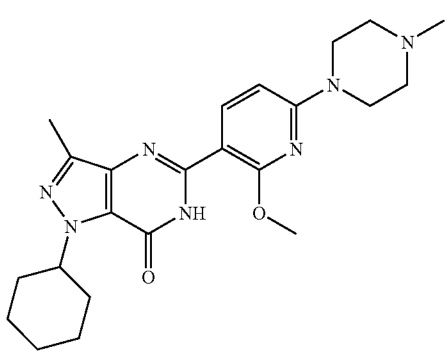 | pale yellow solid 213-215 | CDCl₃ 1.21-1.36(1H, m), 1.41-1.59(2H, m), 1.67-1.76(1H, m), 1.84-2.09(6H, m), 2.35(3H, s), 2.48-2.55(7H, s), 3.65-3.70(4H, m), 4.09(3H, s), 4.95-5.05(1H, m), 6.34(1H, d, J=8.7 Hz), 8.58(1H, d, J=8.7 Hz), 10.81 (1H, brs) | 438 |

TABLE 5

| Example No. | Chemical Structure | Properties m.p.(° C.) (recryst. solvent) | $^1$H-NMR | MS (FAB) (M + 1)$^+$ |
|---|---|---|---|---|
| 17 | 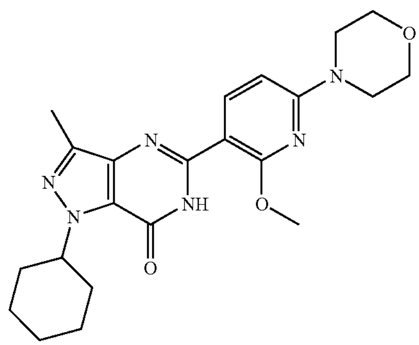 | colorless solid 220-223 | CDCl$_3$ 1.22-1.35(1H, m), 1.41-1.57(2H, m), 1.67-1.75(1H, m), 1.84-2.08(6H, m), 2.52(3H, s), 3.59-3.64(4H, s), 3.80-3.85(4H, m), 4.09(3H, s), 4.95-5.05(1H, m), 6.34(1H, d, J=8.7 Hz), 8.61(1H, d, J=8.7 Hz), 10.80(1H, brs) | 425 |
| 18 | 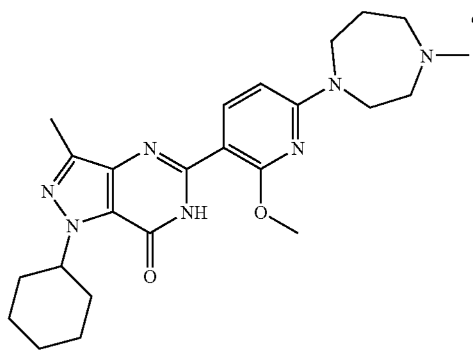 | colorless solid 135-138 | CDCl$_3$ 1.22-1.36(1H, m), 1.41-1.57(2H, m), 1.67-1.75(1H, m), 1.84-2.07(8H, m), 2.39(3H, s), 2.51 (3H, s), 2.54-2.59(2H, m), 2.70-2.75(2H, m), 3.65-3.72(2H, m), 3.81-3.88(2H, m), 4.08(3H, s), 4.94-5.04(1H, m), 6.23(1H, d, J=8.7 Hz), 8.55(1H, d, J=8.7 Hz), 10.82(1H, brs) | 452 |
| 19 | 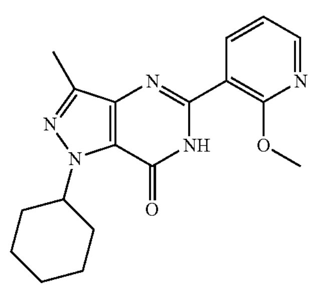 | colorless solid 172-174 (AcOEt/hexane) | CDCl$_3$ 1.21-1.38(1H, m), 1.44-1.58(2H, m), 1.68-1.79(1H, m), 1.85-2.09(6H, m), 2.55(3H, s), 4.19(3H, s), 4.98-5.09(1H, m), 7.13(1H, dd, J=4.9 and 7.7 Hz), 8.31 (1H, dd, J=1.9 and 4.9 Hz), 8.83(1H, dd, J=1.9 and 7.7 Hz), 10.86(1H, brs) | 340 |
| 20 | 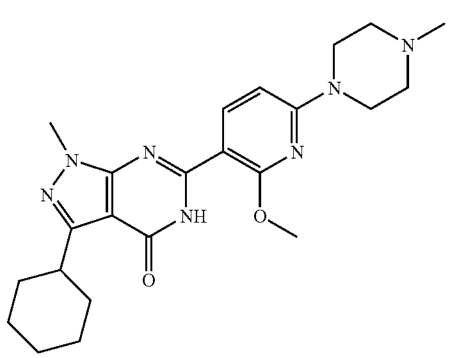 | colorless solid 229.5-232 (EtOH) | CDCl$_3$ 1.26-1.51(3H, m), 1.68-1.87(5H, m), 1.95-2.03(2H, m), 2.35(3H, s), 2.46-2.54(4H, m), 3.01-3.11 (1H, m), 3.64-3.74(4H, m), 3.92(3H, s), 4.09(3H, s), 6.35(1H, d, J=8.8 Hz), 8.59(1H, d, J=8.8 Hz), 10.65(1H, brs) | 438 |

TABLE 6

| Example No. | Chemical Structure | Properties m.p.(° C.) (recryst. solvent) | ¹H-NMR | MS (FAB) (M + 1)⁺ |
|---|---|---|---|---|
| 21 | 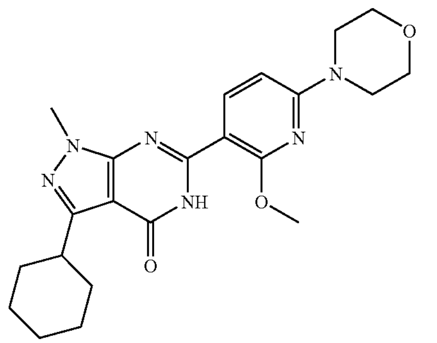 | green/ yellow solid 251.5-255 (EtOH) | CDCl₃ 1.26-1.51(3H, m), 1.69-1.88(5H, m), 1.96-2.04(2H, m), 3.01-3.11(1H, m), 3.60-3.69(4H, m), 3.78-3.86(4H, m), 3.92(3H, s), 4.09(3H, s), 6.34(1H, d, J=8.7 Hz), 8.62(1H, d, J=8.7 Hz), 10.64(1H, brs) | 425 |
| 22 | 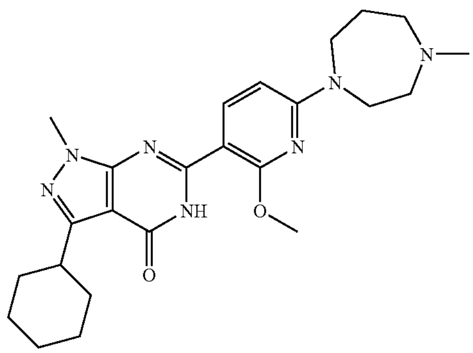 | colorless solid 179.5-180.5 | CDCl₃ 1.28-1.51 (3H, m), 1.68-1.87(5H, m), 1.96-2.09(4H, m), 2.39(3H, s), 2.52-2.61 (2H, m), 2.69-2.79(2H, m), 3.01-3.11 (1H, m), 3.63-3.77(2H, m), 3.80-3.96(2H, m), 3.91(3H, s), 4.08(3H, s), 6.24(1H, d, J=8.7 Hz), 8.57(1H, d, J=8.7 Hz), 10.65(1H, brs) | 452 |
| 23 | 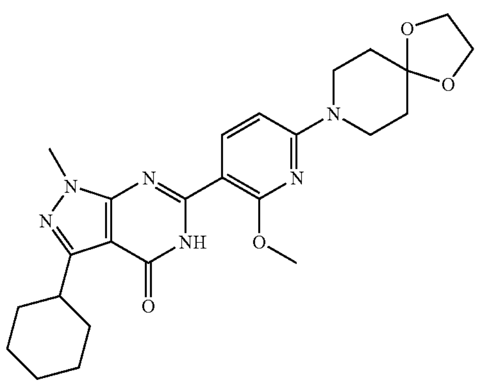 | colorless solid 232.5-234 | CDCl₃ 1.28-1.50(3H, m), 1.69-1.89(9H, m), 1.95-2.05(2H, m), 3.01-3.11(1H, m), 3.73-3.83(4H, m), 3.92(3H, s), 4.00(4H, s), 4.08(3H, s), 6.39(1H, d, J=8.9 Hz), 8.58(1H, d, J=8.9 Hz), 10.65(1H, brs) | 481 |
| 24 | 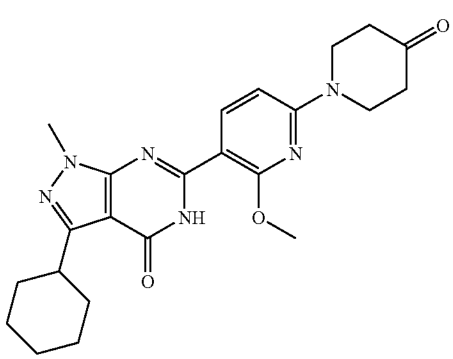 | colorless solid 284-286 AcOEt/EtOH | CDCl₃ 1.28-1.51(3H, m), 1.68-1.88(5H, m), 1.96-2.05(2H, m), 2.53-2.62(4H, m), 3.01-3.11(1H, m), 3.93(3H, s), 3.98-4.07(4H, m), 4.12(3H, s), 6.45(1H, d, J=8.8 Hz), 8.66(1H, d, J=8.8 Hz), 10.62(1H, brs) | 437 |

TABLE 7

| Example No. | Chemical Structure | Properties m.p.(°C.) (recryst. solvent) | ¹H-NMR | MS (FAB) (M + 1)⁺ |
|---|---|---|---|---|
| 25 | (4-hydroxypiperidinyl-pyridine-pyrazolopyrimidinone with cyclohexyl) | colorless solid 205-206.5 (EtOH) | CDCl₃ 1.28-1.50(3H, m), 1.53-1.65(2H, m), 1.69-1.88(5H, m), 1.94-2.04(4H, m), 3.00-3.10(1H, m), 3.30-3.40(2H, m), 3.92(3H, s), 3.94-4.03(1H, m), 4.06-4.17(2H, m), 4.09(3H, s), 6.38(1H, d, J=8.8 Hz), 8.58(1H, d, J=8.8 Hz), 10.65(1H, brs) | 439 |
| 26 | (4-methylaminopiperidinyl-pyridine-pyrazolopyrimidinone with cyclohexyl) | colorless solid 202-203.5 (AcOEt/hexane) | CDCl₃ 1.28-1.63 (5H, m), 1.68-1.87(5H, m), 1.93-2.03(4H, m), 2.47(3H, s), 2.60-2.71 (1H, m), 3.00-3.13(3H, m), 3.91(3H, s), 4.08(3H, s), 4.29-4.39(2H, m), 6.36(1H, d, J=8.8 Hz), 8.57(1H, d, J=8.8 Hz), 10.66(1H, brs) | 452 |
| 27 | (4-dimethylaminopiperidinyl-pyridine-pyrazolopyrimidinone with cyclohexyl) | colorless solid 178.5-180 (EtOH) | CDCl₃ 1.28-1.58(5H, m), 1.68-1.88(5H, m), 1.90-2.03(4H, m), 2.30(6H, s), 2.38-2.48(1H, m), 2.91-3.11(3H, m), 3.91(3H, s), 4.08(3H, s), 4.40-4.50(2H, m), 6.36(1H, d, J=8.8 Hz), 8.57(1H, d, J=8.8 Hz), 10.65(1H, brs) | 466 |
| 28 | (4-aminopiperidinyl-pyridine-pyrazolopyrimidinone with cyclohexyl) | colorless solid 206-208.5 (EtOH) | CDCl₃ 1.27-1.66(5H, m), 1.69-1.87(5H, m), 1.90-2.04(4H, m), 2.93-3.11(4H, m), 3.92(3H, s), 4.03(3H, s), 4.31-4.40(2H, m), 6.37(1H, d, J=8.8 Hz), 8.57(1H, d, J=8.8 Hz), 10.65(1H, brs) | 438 |

TABLE 8

| Example No. | Chemical Structure | Properties m.p.(° C.) (recryst. solvent) | ¹H-NMR | MS (FAB) (M + 1)+ |
|---|---|---|---|---|
| 29 | 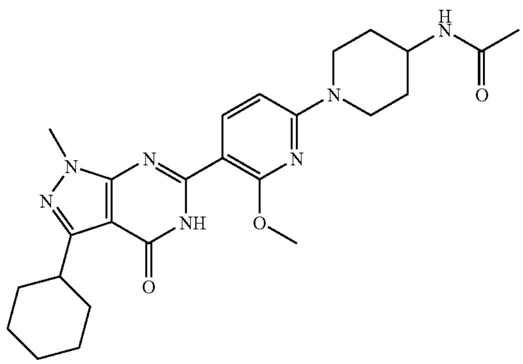 | colorless solid 253.5-255.5 (EtOH) | CDCl₃ 1.24-1.50(5H, m), 1.69-1.88(5H, m), 1.94-2.11(4H, m), 1.98(3H, s), 3.01-3.15(3H, m), 3.92(3H, s), 4.01-4.14(1H, m), 4.08(3H, s), 4.33-4.42(2H, m), 5.30-5.39(1H, m), 6.37(1H, d, J=8.8 Hz), 8.58(1H, d, J=8.8 Hz), 10.63(1H, brs) | 480 |
| 30 | 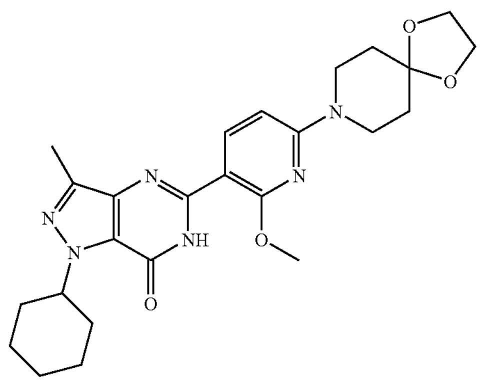 | pale yellow solid 230-232 | CDCl₃ 1.21-1.36(1H, m), 1.41-1.56(2H, m), 1.65-1.80(5H, m), 1.84-2.06(6H, m), 2.51(3H, s), 3.75-3.80(4H, m), 4.00(4H, s), 4.08(3H, s), 4.94-5.04(1H, m), 6.38(1H, d, J=8.8 Hz), 8.57(1H, d, J=8.8 Hz), 10.81(1H, brs) | 481 |
| 31 | 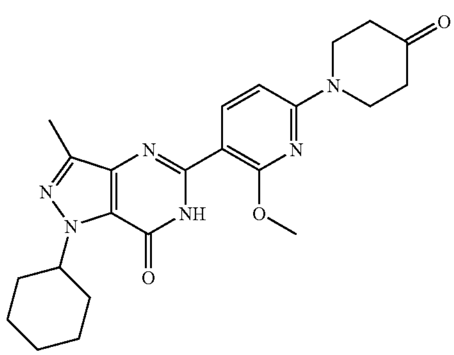 | colorless solid 277-278 (AcOEt/EtOH) | CDCl₃ 1.22-1.36(1H, m), 1.42-1.56(2H, m), 1.69-1.77(1H, m), 1.85-2.10(6H, m), 2.52(3H, s), 2.55-2.61 (4H, m), 3.97-4.03 (4H, m), 4.12(3H, s), 4.94-5.04(1H, m), 6.45(1H, d, J=8.7 Hz), 8.66(1H, d, J=8.7 Hz), 10.77(1H, brs) | 437 |
| 32 | 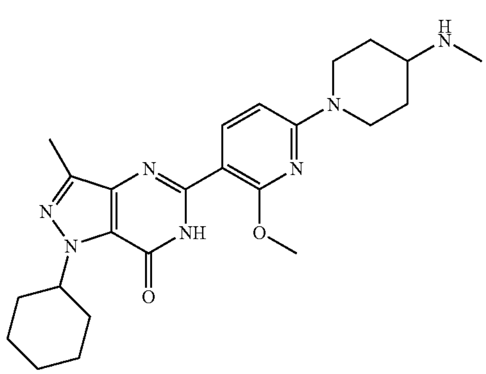 | colorless solid 185-189 (AcOEt/ diisopropyl ether) | CDCl₃ 1.20-1.42(5H, m), 1.66-1.74(1H, m), 1.83-2.06(8H, m), 2.47(3H, s), 2.51(3H, s), 2.60-2.69(1H, m), 3.00-3.09(2H,m), 4.08(3H, s), 4.28-4.36(2H, m), 4.94-5.04(1H, m), 6.36(1H, d, J=8.8 Hz), 8.56(1H, d, J=8.8 Hz), 10.82(1H, brs) | 452 |

TABLE 9

| Example No. | Chemical Structure | Properties m.p.(° C.) (recryst. solvent) | $^1$H-NMR | MS (FAB) (M + 1)$^+$ |
|---|---|---|---|---|
| 33 | 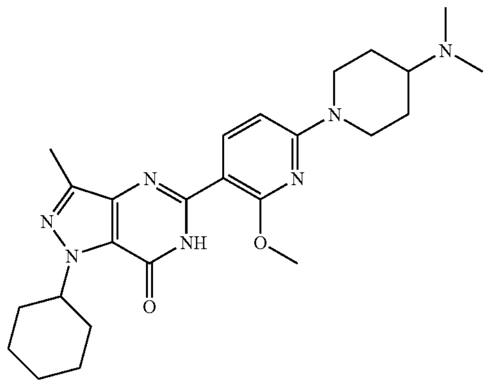 | colorless solid 230-231 (EtOH)/AcOEt | CDCl$_3$ 1.22-1.36(1H, m), 1.42-1.58(4H, m), 1.66-1.75(1H, m), 1.83-2.08(8H, m), 2.30(6H, s), 2.36-2.46(1H, m), 2.51(3H, s), 2.89-2.99(2H, m), 4.08(3H, s), 4.39-4.48(2H, m), 4.95-5.05(1H, m), 6.36(1H, d, J=8.8 Hz), 8.56(1H, d, J=8.8 Hz), 10.82 (1H, brs) | 466 |
| 34 | 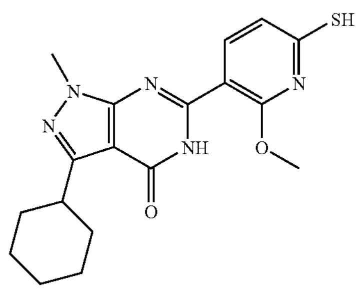 | colorless solid 184(dec.) | CDCl$_3$ 1.28-1.51(3H, m), 1.69-1.91(5H, m), 1.98-2.09(2H, m), 3.03-3.17(1H, m), 3.96(3H, s), 4.15(1H, s), 4.17(3H, s), 7.02(1H, d, J=8.1 Hz), 8.65(1H, d, J=8.1 Hz), 10.62(1H, brs) | 372 |
| 35 | 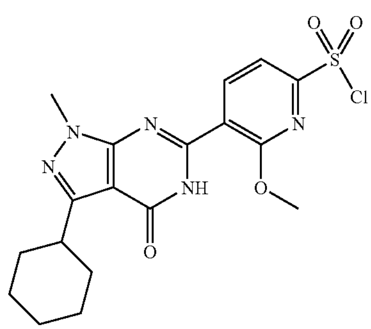 | pale yellow solid 229-232 | CDCl$_3$ 1.28-1.52(3H, m), 1.68-1.90(5H, m), 1.98-2.06(2H, m), 3.04-3.15(1H, m), 3.99(3H, s), 4.33(3H, s), 7.87(1H, d, J=7.8 Hz), 9.12(1H, d, J=7.8 Hz), 10.54(1H, brs) | 438 |
| 36 | 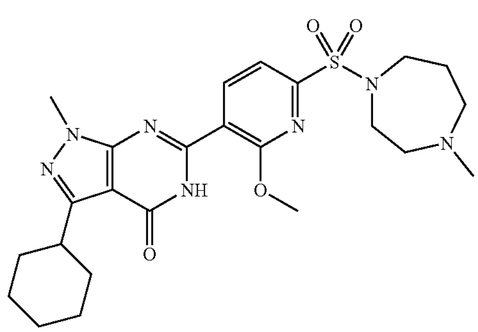 | pale yellow solid 153.5-155.5 (AcOEt/hexane) | CDCl$_3$ 1.22-1.51(3H, m), 1.60-2.04(9H, m), 2.37(3H, s), 2.61-2.72(4H, m), 3.02-3.15(1H, m), 3.53-3.67(4H, m), 3.98(3H, s), 4.22(3H, s), 7.74(1H, d, J=7.8 Hz), 9.00(1H, d, J=7.8 Hz), 10.56(1H, brs) | 516 |

TABLE 10

| Example No. | Chemical Structure | Properties m.p.(° C.) (recryst. solvent) | ¹H-NMR | MS (FAB) (M + 1)⁺ |
|---|---|---|---|---|
| 37 | 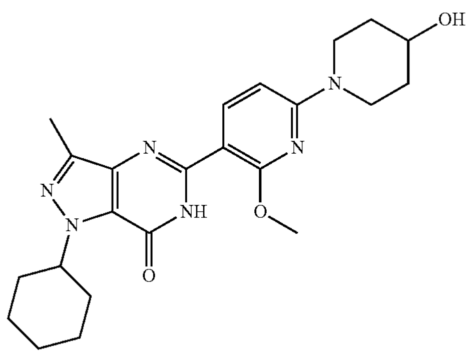 | colorless solid 217-220 | CDCl₃ 1.20-1.35(1H, m), 1.42-1.54(4H, m), 1.68-1.75(1H, m), 1.83-2.08(8H, m), 2.51(3H, s), 3.27-3.35(2H, m), 3.94-4.02(1H, m), 4.09(3H, s), 4.08-4.17(2H, m), 4.94-5.04(1H, m), 6.38(1H, d, J=8.8 Hz), 8.57(1H, d, J=8.8 Hz), 10.81(1H, brs) | 439 |
| 38 | 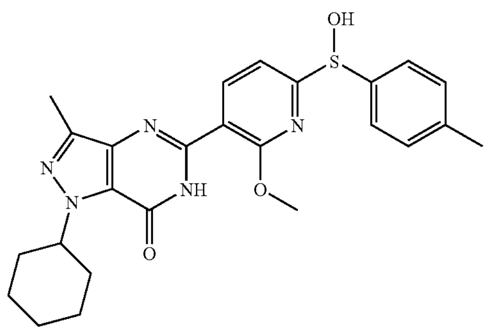 | colorless solid 231-233 (2-butanone) | CDCl₃ 1.21-1.34(1H, m), 1.41-1.57(2H, m), 1.69-1.76(1H, m), 1.85-2.06(6H, m), 2.37(3H, s), 2.52(3H, s), 4.11(3H, s), 4.95-5.06(1H, m), 7.27(2H, d, J=8.1 Hz), 7.67(2H, d, J=8.1 Hz), 7.84(1H, d, J=8.0 Hz), 8.96(1H, d, J=8.0 Hz), 10.59(1H, brs) | 478 |
| 39 | 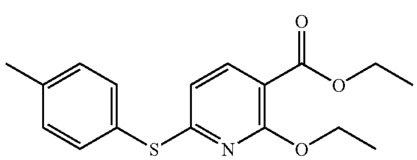 | pale yellow oil | CDCl₃ 1.30(3H, t, J=7.1 Hz), 1.32(3H, t, J=7.1 Hz), 2.39(3H, s), 4.29(2H, q, J=7.1 Hz), 4.32(2H, q, J=7.1 Hz), 6.42(1H, d, J=8.1 Hz), 7.19-7.29(2H, m), 7.43-7.52(2H, m), 7.91 (1H, d, J=8.1 Hz) | 318 |
| 40 | 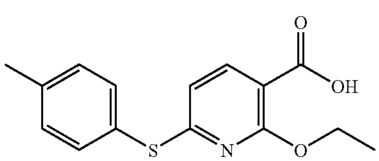 | colorless solid 136.5-140 | CDCl₃ 1.38(3H, t, J=7.1 Hz), 2.41(3H, s), 4.49(2H, q, J=7.1 Hz), 6.58(1H, d, J=8.1 Hz), 7.22-7.30(2H, m), 7.43-7.50(2H, m), 8.14(1H, d, J=8.1 Hz) | 290 |

TABLE 11

| Example No. | Chemical Structure | Properties m.p.(° C.) (recryst. solvent) | ¹H-NMR | MS (FAB) (M + 1)⁺ |
|---|---|---|---|---|
| 41 | 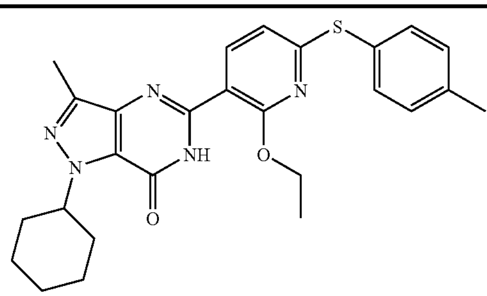 | colorless solid 190-191 (EtOH) | CDCl₃ 1.20-1.35(1H, m), 1.39-1.52(2H, m), 1.42(3H, t, J=7.1 Hz), 1.66-1.76(1H, m), 1.83-2.09(6H, m), 2.41(3H, s), 2.49(3H, s), 4.64(2H, q, J=7.1 Hz), 4.92-5.02(1H, m), 6.63(1H, d, J=8.2 Hz), 7.20-7.28(2H, m), 7.46-7.51(2H, m), 8.57(1H, d, J=8.2 Hz), 10.93(1H, brs) | 476 |

TABLE 11-continued

| Example No. | Chemical Structure | Properties m.p.(° C.) (recryst. solvent) | ¹H-NMR | MS (FAB) (M + 1)⁺ |
|---|---|---|---|---|
| 42 | 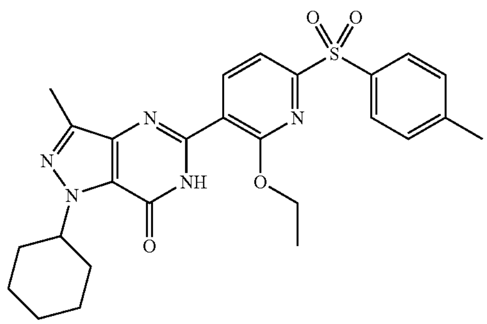 | pale yellow solid 229-230 (EtOH) | CDCl₃ 1.21-1.36(1H, m), 1.40-1.52(2H, m), 1.46(3H, t, J=7.1 Hz), 1.69-1.75(1H, m), 1.86-2.08(6H, m), 2.43(3H, s), 2.53(3H, s), 4.57(2H, q, J=7.1 Hz), 4.94-5.03(1H, m), 7.31-7.38(2H, m), 7.9-7.99(3H, m), 9.00(1H, d, J=8.1 Hz), 10.78(1H, brs) | 508 |
| 43 | 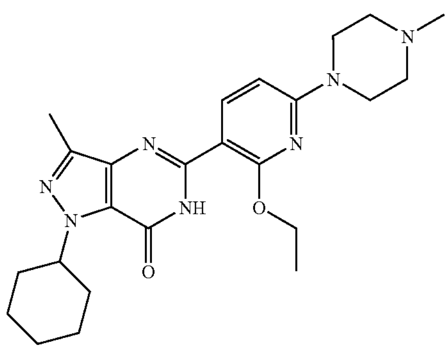 | colorless solid 162.5-163.5 (EtOH) | CDCl₃ 1.21-1.35(1H, m), 1.40-1.57(2H, m), 1.53(3H, t, J=7.1 Hz), 1.67-1.75(1H, m), 1.83-2.09(6H, m), 2.34(3H, s), 2.45-2.57(4H, m), 2.51 (3H, s), 3.60-3.71 (4H, m), 4.56 (2H, q, J=7.1 Hz), 4.93-5.05(1H, m), 6.34(1H, d, J=8.8 Hz), 8.59(1H, d, J=8.8 Hz), 11.02(1H, brs) | 452 |
| 44 | 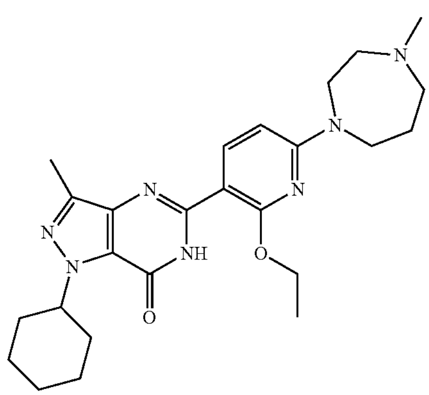 | colorless solid 151-152 (AcOEt/hexane) | CDCl₃ 1.21-1.36(1H, m), 1.40-1.58(2H, m), 1.52(3H, t, J=7.1 Hz), 1.61-1.781H, m), 1.82-2.09(8H, m), 2.38(3H, s), 2.51 (3H, s), 2.54-2.51 (2H, s), 2.69-2.77(2H, m), 3.62-3.73(2H, m), 3.80-3.91 (2H, m), 4.54(2H, q, J=7.1 Hz), 4.92-5.06(1H, m), 6.22(1H, d, J=8.9 Hz), 8.56(1H, d, J=8.9 Hz), 11.02(1H, brs) | 466 |

TABLE 12

| Example No. | Chemical Structure | Properties m.p.(° C.) (recryst. solvent) | ¹H-NMR | MS (FAB) (M + 1)⁺ |
|---|---|---|---|---|
| 45 | 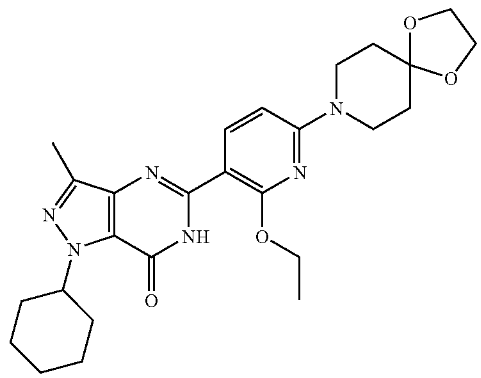 | colorless solid 166-167 | CDCl₃ 1.22-1.38(1H, m), 1.41-1.56(2H, m), 1.52(3H, t, J=7.1 Hz), 1.68-1.79(5H, m), 1.84-2.09(6H, m), 2.51(3H, s), 3.71-3.81(4H, m), 4.00(4H, s), 4.55(2H, q, J=7.1 Hz), 4.92-5.04(1H, m), 6.38(1H, d, J=8.8 Hz), 8.57(1H, d, J=8.8 Hz), 11.01(1H, brs) | 495 |
| 46 | 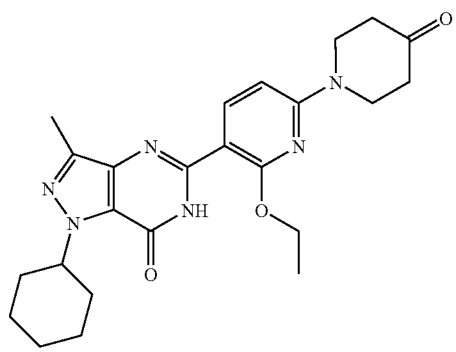 | colorless solid 220-221 (AcOEt) | CDCl₃ 1.21-1.36(1H, m), 1.40-1.59(2H, m), 1.55(3H, t, J=7.1 Hz), 1.67-1.79(1H, m), 1.84-2.10(6H, m), 2.52(3H, s), 2.53-2.61(4H, m), 3.94-4.04(4H, m), 4.58(2H, q, J=7.1 Hz), 4.91-5.03(1H, m), 6.45(1H, d, J=8.7 Hz), 8.66(1H, d, J=8.7 Hz), 10.97(1H, brs) | 451 |
| 47 | 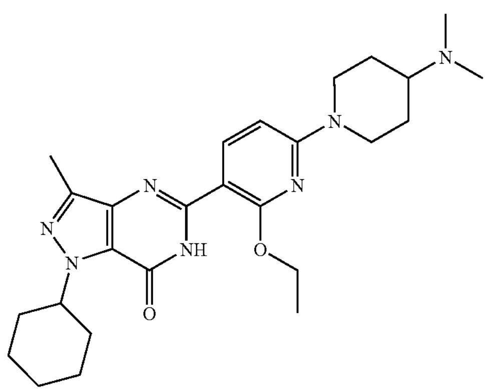 | colorless solid 186-186.5 (EtOH) | CDCl₃ 1.22-1.39(1H, m), 1.41-1.59(4H, m), 1.54(3H, t, J=7.1 Hz), 1.68-1.77(1H, m), 1.85-2.10(8H, m), 2.31(6H, s), 2.35-2.49(1H, m), 2.53(3H, s), 2.89-3.00(2H, m), 4.38-4.49(2H, m), 4.57(2H, q, J=7.1 Hz), 4.97-5.08(1H, m), 6.37(1H, d, J=8.8 Hz), 8.58(1H, d, J=8.8 Hz), 11.03(1H, brs) | 480 |
| 48 | 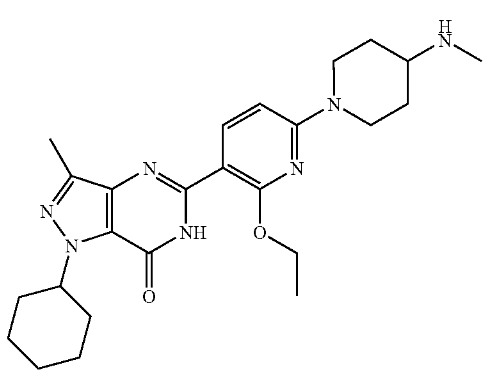 | colorless solid 155-156.5 (AcOEt/hexane) | CDCl₃ 1.22-1.62(5H, m), 1.54(3H, t, J=7.1 Hz), 1.69-1.78(1H, m), 1.86-2.10(8H, m), 2.48(3H, s), 2.53(3H, s), 2.61-2.70(1H, m), 3.00-3.10(2H, m), 4.27-4.38(2H, m), 4.57(2H, q, J=7.1 Hz), 4.96-5.08(1H, m), 6.37(1H, d, J=8.8 Hz), 8.58(1H, d, J=8.8 Hz), 11.04(1H, brs) | 466 |

TABLE 13

| Example No. | Chemical Structure | Properties m.p.(° C.) (recryst. solvent) | $^1$H-NMR | MS (FAB) (M + 1)$^+$ |
|---|---|---|---|---|
| 49 | 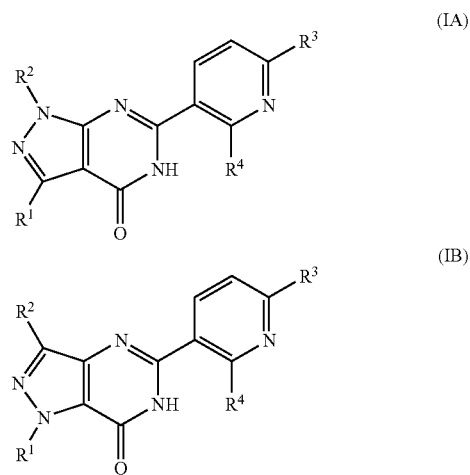 | colorless solid 198-199 (EtOH) | CDCl$_3$ 1.22-1.37(1H, m), 1.41-1.65(4H, m), 1.54(3H, t, J=7.1 Hz), 1.68-1.78(1H, m), 1.86-2.10(8H, m), 2.53(3H, s), 3.26-3.31(2H, m), 3.94-4.03(1H, m). 4.07-4.16(2H, m), 4.57(2H, q, J=7.1 Hz), 4.94-5.05(1H, m), 6.38(1H, d, J=8.8 Hz), 8.59(1H, d, J=8.8 Hz), 11.03(1H, brs) | 453 |

INDUSTRIAL APPLICABILITY

The compounds of the present invention inhibit PDE 7 selectively, and therefore, enhance cellular cAMP level. Consequently, the compounds of the present invention are useful for treating various kinds of disease such as allergic disease, inflammatory disease or immunologic disease.

That is, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, GVH disease, and restenosis after angioplasty.

The invention claimed is:

1. A pyridinylpyrazolopyrimidinone compound represented by the following formula (IA) or (IB):

(IA)

(IB)

wherein:

$R^1$ is an optionally substituted $C_3$-$C_8$ cycloalkyl group or tert-butyl group;

$R^2$ is a hydrogen atom or $C_1$-$C_3$ alkyl group;

$R^3$ is —$NR^5R^6$, —C(=O)$R^7$ or —S(O)$_{0-2}R^8$;

$R^4$ is a hydrogen atom or $C_1$-$C_3$ alkoxyl group which is optionally substituted by one or more fluorine atom(s);

$R^5$ and $R^6$ are, same or different from each other, a hydrogen atom, optionally substituted $C_1$-$C_6$ alkyl group, optionally substituted acyl group, optionally substituted heterocycloalkyl group, and optionally substituted heterocycloalkyl ring which is formed with the nitrogen atom binding $R^5$ and $R^6$;

$R^7$ is —$OR^9$ or —$NR^5R^6$;

$R^8$ is a hydrogen atom, a halogen atom, —$NR^5R^6$, unsubstituted $C_1$-$C_6$ alkyl group, or optionally substituted aryl group;

$R^9$ is a hydrogen atom or optionally substituted $C_1$-$C_6$ alkyl group;

or pharmaceutically acceptable salts thereof.

2. The compound represented by the formula (IA) according to claim 1.

3. The compound represented by the formula (IB) according to claim 1.

4. The compound according to claim 1, in which $R^1$ is cyclohexyl group or cycloheptyl group.

5. The compound according to claim 1, in which $R^2$ is methyl group.

6. The compound according to claim 1, in which $R^4$ is methoxy or ethoxy group.

7. The compound according to claim 1, in which $R^3$ is a group —$NR^5R^6$.

8. A pharmaceutical composition comprising a compound according to claim 1, or pharmaceutically acceptable salts thereof as the active ingredient.

\* \* \* \* \*